(12) United States Patent
Yung et al.

(10) Patent No.: US 10,383,959 B2
(45) Date of Patent: Aug. 20, 2019

(54) DUAL-MODE CONTRAST AGENT AND USES THEREOF IN REAL-TIME MONITORING AND HARVESTING OF NEURAL STEM CELLS

(71) Applicant: Hong Kong Baptist University, Hong Kong (HK)

(72) Inventors: Kin Lam Yung, Hong Kong (HK); Nga Ping Lui, Hong Kong (HK); Shik Chi Tsang, Hong Kong (HK); Yung Kang Peng, Hong Kong (HK)

(73) Assignee: Hong Kong Baptist University, Hong Kong (HK)

( * ) Notice: Subject to any disclaimer, the term of this patent is extended or adjusted under 35 U.S.C. 154(b) by 261 days.

(21) Appl. No.: 14/804,348

(22) Filed: Jul. 21, 2015

(65) Prior Publication Data
US 2015/0335767 A1 Nov. 26, 2015

Related U.S. Application Data

(63) Continuation-in-part of application No. 13/834,750, filed on Mar. 15, 2013, now Pat. No. 9,109,203.

(60) Provisional application No. 62/051,298, filed on Sep. 16, 2014.

(51) Int. Cl.
| | |
|---|---|
| *A61B 5/055* | (2006.01) |
| *A61K 49/18* | (2006.01) |
| *C12N 5/0797* | (2010.01) |
| *B82Y 15/00* | (2011.01) |

(52) U.S. Cl.
CPC ........ *A61K 49/183* (2013.01); *A61K 49/1875* (2013.01); *C12N 5/0623* (2013.01); *A61K 49/1824* (2013.01); *B82Y 15/00* (2013.01)

(58) Field of Classification Search
None
See application file for complete search history.

(56) References Cited

U.S. PATENT DOCUMENTS

2011/0070202 A1   3/2011   Yarowsky et al.

FOREIGN PATENT DOCUMENTS

| CN | 1850966 A | 10/2006 |
|---|---|---|
| CN | 101503623 A | 8/2009 |

OTHER PUBLICATIONS

Yang et al. (Biomater. 2011, 32, 4584-4593).*
Chen et al. (Biomater. 2012, 33, 2388-2398).*
Chen et al. (Biomater. 2012, 33, 7126-7137).*
Gamarra et al. (Int. J. Nanomed. 2010, 5, 203-211).*
Choi et al. (J. Am. Chem. Soc. 2010, 132, 11015-11017).*
Suteewong et al. (Chem. Mater. 2012, 24, 3895-3905).*
Doetsch et al., "Cellular Composition and Three-Dimensional Organization of the Subventricular Germinal Zone in the Adult Mammalian Brain", The Journal of Neuroscience, Jul. 1, 1997, 17(13):5046-5061.
M.W. Brightman, S. L. Palay, "The Fine Structure of Ependyma in the Brain of the Rat", The Journal of cell biology, 19, 415 (Nov. 1963).
C. Lee et al., The molecular profiles of neural stem cell niche in the adult subventricular zone, PLOS One 7, e50501 (2012).
Du Y. et al., "Isolation and purification of the Human Embryonic Neural Stem Cells with Immunomagnetic method" Journal of Zhengzhou University (Medical Sciences). Jan. 2003, vol. 38, No. 1, pp. 13-15.
Galanzha Ekaterina I et. al., "In vivo magnetic enrichment and multipliex photoacoustic detection of circulating tumore cells" Nature Nanotechnology, Nature Publishing Group, GB, vol. 4, No. 12, Dec. 1, 2009, pp. 855-860.
Schreiber HA (2010) "Using carbon magnetic nanoparticles to target, track, and manipulate dendritic cells" Journal of immunological methods 356 (1-2).
Supplementary European search report of 13855417.5 issued from the EPO dated Aug. 6, 2016.

* cited by examiner

*Primary Examiner* — Michael G. Hartley
*Assistant Examiner* — Melissa J Perreira
(74) *Attorney, Agent, or Firm* — Spruson & Ferguson (Hong Kong) Limited

(57) ABSTRACT

A real-time method to monitor and harvest stem cells is provided in the present invention. In particular, the present invention provides a real-time method to monitor and harvest neural stem cells. The present invention has applications in providing an individualized cell replacement therapy for patient in need thereof. More specifically, the present invention has applications in performing real-time monitoring and harvesting of neural stem cells using magnetic resonance imaging (MRI).

15 Claims, 15 Drawing Sheets

(A)

(B)

DUAL-MODE CONTRAST AGENT AND USES THEREOF IN REAL-TIME MONITORING AND HARVESTING OF NEURAL STEM CELLS

CROSS-REFERENCE TO RELATED APPLICATIONS

This application is a continuation-in-part application of U.S. Non-Provisional patent application Ser. No. 13/834,750 filed Mar. 15, 2013, which claims the benefit of U.S. Provisional Patent Application Ser. No. 61/726,762 filed Nov. 15, 2012, and claims benefit of U.S. Provisional Patent Application Ser. No. 62/051,298 filed Sep. 16, 2014, and the disclosures of which are hereby incorporated by reference in their entirety.

FIELD OF INVENTION

The present invention relates to a real-time method to monitor and harvest stem cells. In particular, the present invention provides a real-time method to monitor and harvest neural stem cells. The present invention has applications in providing an individualized cell replacement therapy for patient in need thereof. More specifically, the present invention has applications in performing real-time monitoring and harvesting of neural stem cells using magnetic resonance imaging (MRI).

BACKGROUND OF INVENTION

Research in regenerative medicine has established a substantial progress in recent years. The development of novel stem-cell-based therapies becomes an exciting and fast moving trend in the field. Many neurological diseases, such as Parkinson's disease, Alzheimer's disease and stroke, involved massive cell loss. Cell replacement could possibly be the only way to reverse this devastating condition. However, the sources of stem cell have given rise to much of the controversy. Embryonic stem cell (ESCs) and induced pluripotent stem cell (iPSCs) have shown an outstanding potential in differentiation into specialized cells of all three germ layers, i.e. ectoderm, mesoderm and endoderm. Given that their pluripotency provides a great interest in basic researches and clinical applications, they bring out heated arguments on the ethical concerns, immunogenicity and a high incidence of tetratoma formation. The safety of using these cells in regenerative medicine should be carefully evaluated. To develop an effective and safe stem cell-based therapy, adult neural stem cells (ANCSs) offer an alternative candidate. Nonetheless, there is no safe and easy way of real-time monitoring and harvesting the ANCS in a live animal or in human. It is one objective of the present invention to provide a real-time method to monitor and harvest neural stem cells in an integrated system.

SUMMARY OF INVENTION

In accordance with a first aspect of the present invention, there is provided a real-time method to monitor and harvest stem cells. In particular, the present invention provides a real-time method to monitor and harvest neural stem cells. The present invention has applications in providing an individualized cell replacement therapy for patient in need thereof. More specifically, the present invention has applications in performing real-time monitoring and harvesting of neural stem cells using magnetic resonance imaging (MRI).

In accordance with a second aspect of the present invention, there is provided a contrast agent that can both perform real-time imaging and real-time harvesting of neural stem cells using a magnetic based imaging tool, wherein said contrast agent exhibits characteristics comprising strong relaxation property for high contrast imaging; strong magnetic susceptibility for magnetic isolation of neural stem cells; can specifically target and attach to neural stem cells; can harvest said specifically targeted neural stem cells, and high biocompatibility in the human body.

In a first embodiment of the second aspect of the present invention, there is provided a contrast agent, wherein said magnetic based imaging tool is a magnetic resonance imaging (MRI) apparatus.

In a second embodiment of the second aspect of the present invention, there is provided a contrast agent, wherein said contrast agent comprises at least one component of a T1 contrast agent and/or at least one component of a T2 contrast agent.

In a third embodiment of the second aspect of the present invention, there is provided a contrast agent, wherein said at least one component of T1 contrast agent comprises manganese (Mn) based contrast agents.

In a fourth embodiment of the second aspect of the present invention, there is provided a contrast agent, wherein said at least one component of T1 contrast agent further comprises magnesium oxide (MnO) based contrast agents.

In a fifth embodiment of the second aspect of the present invention, there is provided a contrast agent, wherein said at least one component of T2 contrast agent comprises superparamagnetic iron oxide nanoparticles (SPIONPs) based contrast agents.

In a sixth embodiment of the second aspect of the present invention, there is provided a contrast agent, wherein said at least one component of T2 contrast agent further comprises magnetite ($Fe_3O_4$) and maghemite ($Fe_2O_3$) based contrast agents.

In a seventh embodiment of the second aspect of the present invention, there is provided a contrast agent, wherein said contrast agent is added to at least one porous silica shell.

In an eighth embodiment of the second aspect of the present invention, there is provided a contrast agent, wherein said at least one porous silica shell comprises mesoporous silica ($mSiO_2$).

In a ninth embodiment of the second aspect of the present invention, there is provided a contrast agent, wherein said at least one porous silica shell further comprises at least three distinct topological domains which can be independently functionalized, such as: at least one hollow interior core; one or more worm-like nanochannels; and a silica outmost surface.

In a tenth embodiment of the second aspect of the present invention, there is provided a contrast agent, wherein the at least one hollow interior core is functionalized with at least one component of the T2 contrast agent.

In an eleventh embodiment of the second aspect of the present invention, there is provided a contrast agent, wherein the one or more worm-like nanochannels are functionalized with at least one component of the T1 contrast agent.

In a twelfth embodiment of the second aspect of the present invention, there is provided a contrast agent, wherein the silica outmost surface is functionalized with anti-CD133 antibodies for specific neural stem cells targeting.

In a first embodiment of the third aspect of the present invention, there is provided a process of synthesizing the contrast agent of the present invention, wherein at least one component of a T2 contrast agent is functionalized in at least one hollow interior core of at least one porous silica shell; at least one component of a T1 contrast agent is functionalized in one or more worm-like nanochannels of the at least one porous silica shell, and anti-CD133 antibodies are functionalized on the outer surface of the at least one porous silica shell.

In a second embodiment of the third aspect of the present invention, there is provided a process of synthesizing the contrast agent of the present invention, wherein said at least one component of T2 contrast agent comprises superparamagnetic iron oxide nanoparticles (SPIONPs) based contrast agents.

In a third embodiment of the third aspect of the present invention, there is provided a process of synthesizing the contrast agent of the present invention, wherein said at least one component of T2 contrast agent further comprises magnetite ($Fe_3O_4$) and maghemite ($Fe_2O_3$) based contrast agents.

In a fourth embodiment of the third aspect of the present invention, there is provided a process of synthesizing the contrast agent of the present invention, wherein said at least one component of T1 contrast agent comprises manganese (Mn) based contrast agents.

In a fifth embodiment of the third aspect of the present invention, there is provided a process of synthesizing the contrast agent of the present invention, wherein said at least one component of T1 contrast agent further comprises magnesium oxide (MnO) based contrast agents.

In a sixth embodiment of the third aspect of the present invention, there is provided a process of synthesizing the contrast agent of the present invention, wherein said at least one porous silica shell comprising mesoporous silica ($mSiO_2$).

In a first embodiment of the fourth aspect of the present invention, there is provided a method for performing real-time imaging and real-time harvesting of neural stem cells comprising using the contrast agent of the present invention.

In a second embodiment of the fourth aspect of the present invention, there is provided a method for performing real-time imaging and real-time harvesting of neural stem cells comprising using the contrast agent of the present invention, wherein said magnetic based imaging tool is a magnetic resonance imaging (MRI) apparatus.

Those skilled in the art will appreciate that the invention described herein is susceptible to variations and modifications other than those specifically described.

The invention includes all such variation and modifications. The invention also includes all of the steps and features referred to or indicated in the specification, individually or collectively, and any and all combinations or any two or more of the steps or features.

Other aspects and advantages of the invention will be apparent to those skilled in the art from a review of the ensuing description.

BRIEF DESCRIPTION OF DRAWINGS

The above and other objects and features of the present invention will become apparent from the following description of the invention, when taken in conjunction with the accompanying drawings, in which:

in FIG. 1(A), from left to right panels: 7 nm $Fe_3O_4$ nanoparticles (NPs), $Fe_3O_4@SiO_2$-CD133 [$Fe_3O_4@SiO_2$ with the conjugation of anti-CD133 antibody (T2 SPIONs-based contrast agent)], MnO@mSiO$_2$-CD133 [MnO/mSiO$_2$-CD133 with the conjugation of anti-CD133 antibody (T1 Mn-based contrast agent)], $Fe_3O_4$@MnO/mSiO$_2$-CD133 [$Fe_3O_4$@MnO/mSiO$_2$-CD133 with the conjugation of anti-CD133 antibody (T1/T2 dual-mode contrast agent)]; in FIG. 1(B); ex-situ T1-T2 MRI studies of the three different CAs (i.e., $Fe_3O_4@SiO_2$-CD133, MnO@mSiO$_2$-CD133, and $Fe_3O_4$@MnO/mSiO$_2$-CD133).

DETAILED DESCRIPTION OF INVENTION

The present invention is not to be limited in scope by any of the specific embodiments described herein. The following embodiments are presented for exemplification only.

Without wishing to be bound by theory, the present invention provides a real-time method to monitor and harvest stem cells. In particular, the present invention provides a real-time method to monitor and harvest neural stem cells. The present invention has applications in providing an individualized cell replacement therapy for patient in need thereof. More specifically, the present invention has applications in performing real-time monitoring and harvesting of neural stem cells using magnetic resonance imaging (MRI).

The recent discovery of the adult neurogenesis gives a strong evidence of the existence of functional neural stem cells (NSCs) in adulthood. The multipotent adult NSCs are capable of self-renewing and continuously generating different neuronal phenotypes in the ventricular-subventricular zone (V-SVZ) and subgranular zone (SGZ) of the hippocampus. Notably, V-SVZ is the largest adult neurogenic niche with a special cytoarchitecture for producing olfactory bulb interneurons and oligodendrocytes. In an early work in Lui C. N. P., Tsui Y. P., Ho A. S. L., Shum D. K. Y, Chan Y. S., Wu C. T., Li H. W., Tsang S. C. E. and Yung K. K. L. (2013). "Neural Stem Cells Harvested from Live Brains by Antibody-Conjugated Magnetic Nanoparticles." *Angew. Chem. Int. Ed,* 52: 12298-12302, where the disclosure of which is incorporated by reference in its entirety, the authors have performed in situ and safely extracted the magnetic ($Fe_3O_4$) nanoparticle (NPs) tagged CD133 positive stem cells from the ependymal layers lining the V-SVZ in living adult rodent models by manipulating the magnetic field. Neurospheres and several differentiated neuronal phenotypes can be produced from the extracted stem cells. The present invention provides that the patients can utilize the NSCs originated from them for an individualized cell replacement therapy with this technology. Ethical issues and risk of immune response can be prospectively overcome. However, to perfect the technology for the translational approach, the present invention has to address the exact location of stem cells in the brain and monitor the whole isolation process. Magnetic resonance imaging (MRI) can assist in optimizing and parameterizing of this approach. Since the $Fe_3O_4$ NPs probe used in referenced patent of U.S. Non-Provisional patent application Ser. No. 13/834,750 filed Mar. 15, 2013, which claims the benefit of U.S. Provisional Patent Application Ser. No. 61/726,762 filed Nov. 15, 2012 not only able to respond to external magnetic field but also has been widely used in clinical magnetic resonance imaging (MRI), MRI is the best choice that can assist us to monitor the time course distribution and the collection process of targeted stem cells in a living rat brain.

Figure 1:
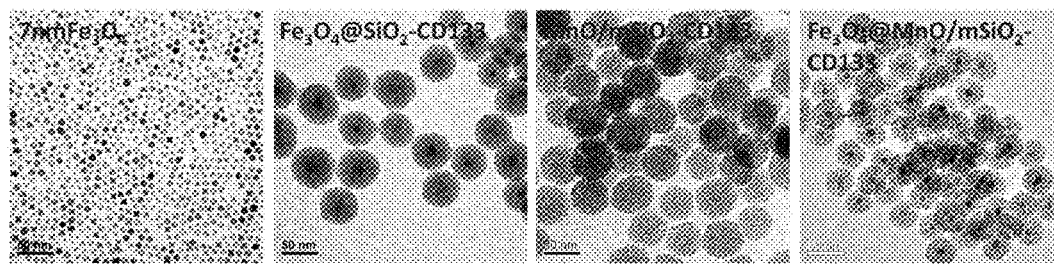
FIG. 1 shows (A) the transmission electron microscopy (TEM) and (B) the ex-situ MRI studies of different contrast agents.
Figure 1:
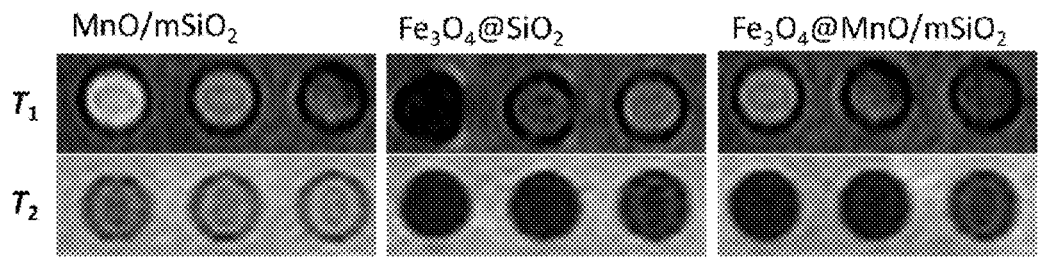

MRI has long been known as a high-valued and non-invasive diagnostic technique with its high imaging flexibility, non-ionizing modality, unlimited depth of tissue penetration and wide acceptance from the patients. This technique could enable to analyze the tomographic images of tagged NSCs and monitor the harvest of the NSCs in the subject's brain alive with a high spatial and temporal resolution in real time. The contrast agents of the present invention are configured to improve the sensitivity by changing the proton relaxation rate. The visualization of the differences between background and labeled stem cells can therefore be enhanced with contrast agents. T1 and T2 contrast agents of the present invention are shown in FIG. 1, where the T1 contrast agents comprise paramagnetic species (i.e. $Gd_2O_3$, MnO) for facilitating spin-lattice relaxation of protons from nearby water molecules to give a positive (bright) MRI image. While the T2 contrast agents consist of superparamagnetic nanoparticles (SPIONPs) which cause protons in vicinity to undergo spin-spin relaxation that gives rise to negative (dark) MRI image and magnetic moment, however, the strong and long-range magnetic field effect will cause MRI image blurring due to excessive T2 influence. To achieve the present invention that is applicable on both real-time monitoring and harvesting of NSCs, a novel contrast agent is employed (FIG. 1) with a perfect combination of the unique strengths of T1 (strong relaxation property for high contrast imaging) and T2 (strong magnetic susceptibility for in situ magnetic isolation of NSCs). Silica coating is also introduced to the contrast agent of the present invention for the functionalization strategy, i.e. coupling of specific stem cell marker antibodies for tracking NSCs. Contrast agents (CAs), generally classified into T2-weighted ($r_2/r_1$ ratio>>1) and T1-weighted CAs ($r_2/r_1$ ratio close to 1), have been widely applied to increase MR tissue contrast.

For T2 CAs of the present invention, superparamagnetic iron oxide nanoparticles (SPIONPs), which generate an induced magnetic field under an external field, perturbs the spin-spin relaxation processes of water protons in vicinity giving rise to negative (dark) MRI image. However, the induced long range magnetic field and the susceptibility artifacts distort the background image, which could mislead the clinical diagnosis in T2-weighted MRI. In contrast, T1 CAs comprise paramagnetic species (i.e. $Gd_2O_3$, MnO) for facilitating spin-lattice relaxation of nearby water protons have been regarded as an advantageous alternative as they can provide positive (bright) MRI image. However, such single mode contrast is not yet perfect and is increasingly facing challenges especially when accurate imaging of small biological targets is needed. Even though the undesirable quenching of the T1 signal has been reported when the relaxation process of the T1 CA is perturbed by the magnetic field generated by a $T_2$ CA, a MRI CA combining both T1 (Gd-complex or $Gd_2O(CO_3)_2$ shell) and T2 ($Fe_3O_4$ NP) dual-modal (DM) imaging in a single unit has recently been demonstrated to be able to give highly accurate information. Unfortunately, Gd-based (e.g. Gd-complexes, $Gd_2O_3$ NPs) T1 CAs are hazardous once if they dissociate and accumulate in the body, limiting their clinical applications. All of the clinical available Gd-based contrast agents are associated with life-threatening nephrogenic systemic fibrosis that is believed to result from transmetallation and retention of Gd(III) in the human body. It is therefore urgent to develop a new dual-mode contrast agents (DMCAs) with both superior contrast and high biocompatibility.

Figure 2A:
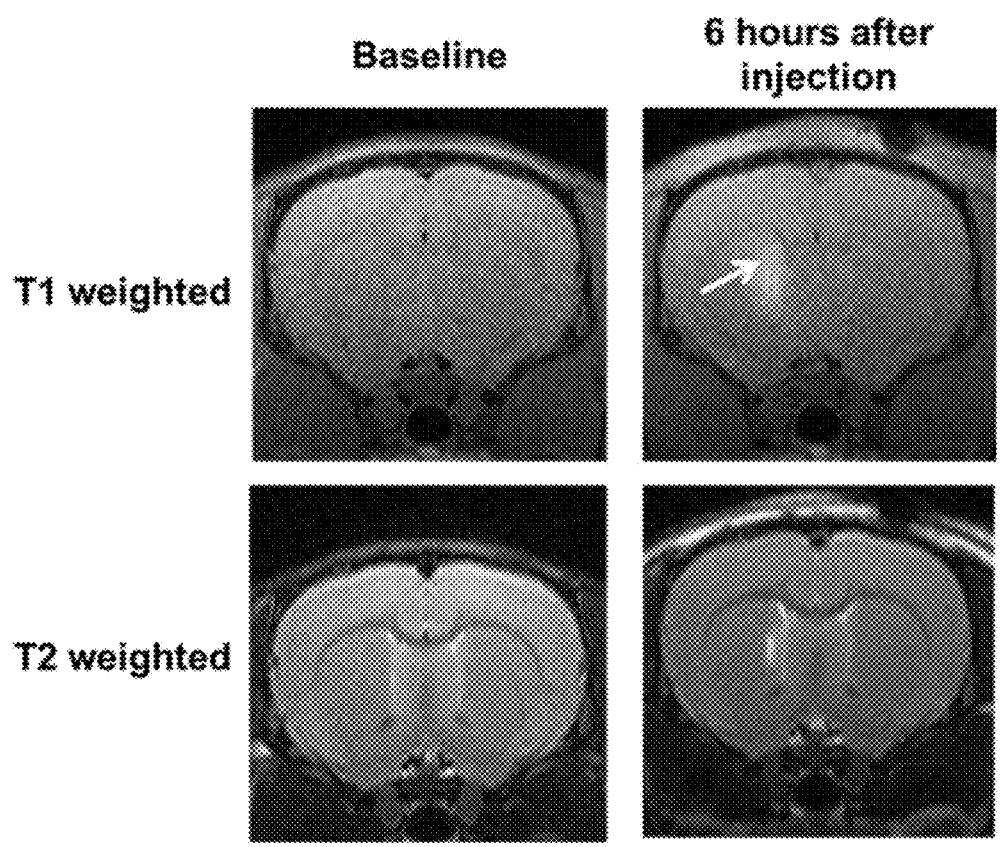
FIG. 2a shows in-situ T1 contrast core-shell nanoparticles-stem cells from a rat subject. The contrast core-shell nanoparticles used in this example is MnO-based T1 CAs of the present invention. The CAs are unilaterally injected into the left V-SVZ for the tracking of the CD133$^+$ NSCs. After 6 hour-incubation, the CAs are able to specifically label the cells for the harvest. The arrow indicates the regions of interest.
Figure 2B:
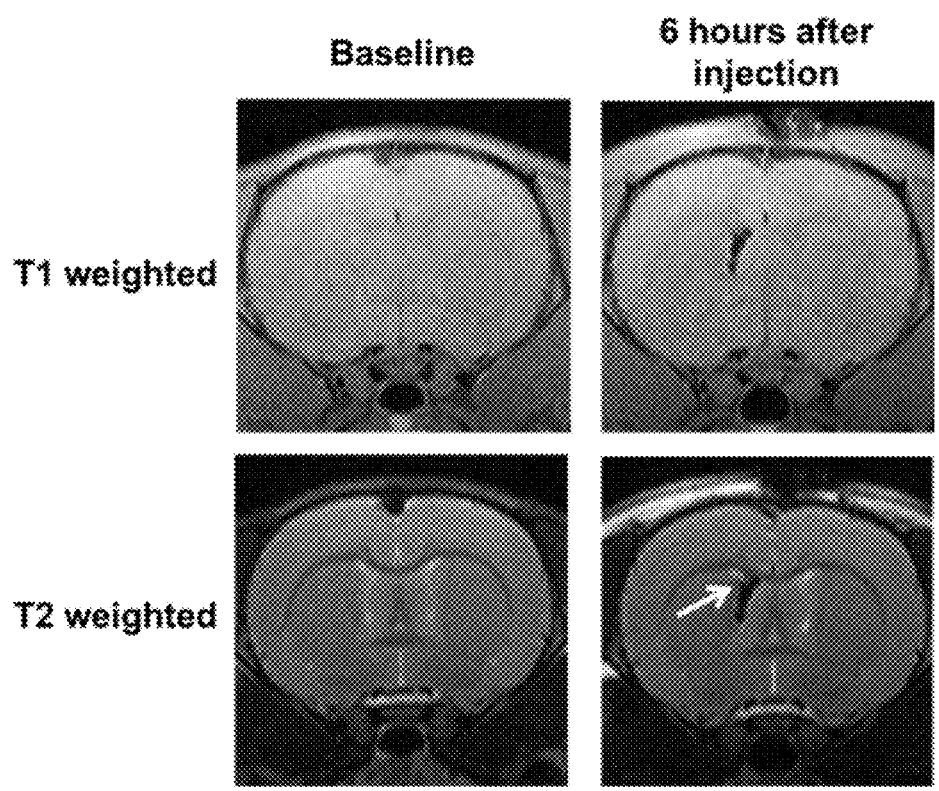
FIG. 2b shows in-situ T2 contrast core-shell nanoparticles-stem cells from a rat subject. The contrast core-shell nanoparticles used in this example is $Fe_3O_4$-based T2 CAs of the present invention. The CAs are unilaterally injected into the left V-SVZ for the tracking of the CD133$^+$ NSCs. After 6 hour-incubation, the CAs are able to specifically label the cells for the harvest. The arrow indicates the regions of interest.

Manganese (Mn) has been recently received special attention as versatile T1 positive contrast agents. They are thermodynamically stable, water-soluble and with an efficient $r_1$ enhancement. Comparing with the T2 SPIONPs like magnetite ($Fe_3O_4$) and maghemite ($Fe_2O_3$), the Mn-based T1 contrast agents exhibit clear and bright images for outstanding accuracy. The inventors unilaterally injected both of the T1 and T2 contrast agents (2000 ug mL$^{-1}$ in 5 mL of PBS) into the V-SVZ respectively [please see FIG. 2a; FIG. 2b]. With the immobilization of the anti-CD133 antibodies on the contrast agents, they could specifically localize to NSCs of V-SVZ and no dispersal of the particles could be observed in the brain. The spatial distribution of the particles is monitored 6 hours after the injection where extensive binding of the particles to the NSCs has been shown in Lui C. N. P., Tsui Y. P., Ho A. S. L., Shum D. K. Y, Chan Y. S., Wu C. T., Li H. W., Tsang S. C. E. and Yung K. K. L. (2013) "Neural Stem Cells Harvested from Live Brains by Antibody-Conjugated Magnetic Nanoparticles." *Angew. Chem. Int. Ed,* 52: 12298-12302, where the disclosure of which is incorporated herein by reference in its entirety. In agreement with the literature, a positive contrast can be noticed in the T1-weighted MRI but not in the T2-weighted MRI when using the Mn-based contrast agent (FIG. 2a). As expected, SPIONPs would have dark effect on MRI (FIG. 2b). There is no doubt that using T1 contrast agent can avoid the mis-interpretation of the MRI images due to the negative contrast which often confuse with the low-level MIR signal from adjacent tissues, including bone or vasculature of brain. As concerning that V-SVZ is located in close proximity to blood vessel scaffold, the T1 contrast agent can eliminate this drawback and satisfy the invention's need for an effective labeling and accurate tracking of NSCs.

Figure 3A:
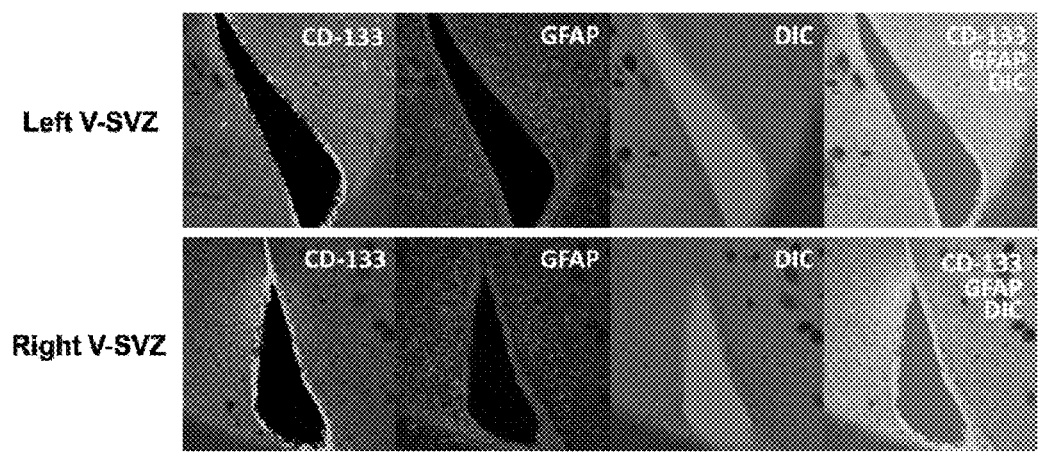
FIG. 3a shows the efficiency of neural stem cell detachment with T1 contrast agent (MnO-based T1 CA) under the magnetic field from MRI machine. The CAs are unilaterally injected into the left V-SVZ. With the external magnetic field generated from the MRI, a magnetic agitation for the CD133$^+$ NSCs harvest can be performed.
Figure 3B:
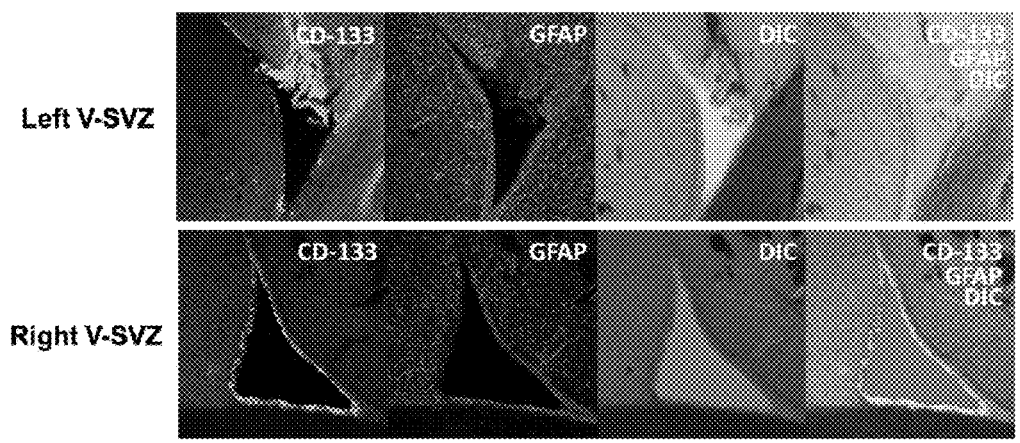
FIG. 3b shows the efficiency of neural stem cell detachment with T2 contrast agent ($Fe_3O_4$-based T2 CA) under the magnetic field from MRI machine. The CAs are unilaterally injected into the left V-SVZ. With the external magnetic field generated from the MRI, a magnetic agitation for the CD133$^+$ NSCs harvest can be performed. An effective detachment of the NSCs from the choroid plexus lining along the V-SVZ can be noticed with the $Fe_3O_4$-based T2 CA but severe damages can be observed with the $Fe_3O_4$-based T2 CA.

It has been previously demonstrated in Lui C. N. P., Tsui Y. P., Ho A. S. L., Shum D. K. Y., Chan Y. S., Wu C. T., Li H. W, Tsang S. C. E. and Yung K. K. L. (2013). "Neural Stem Cells Harvested from Live Brains by Antibody-Conjugated Magnetic Nanoparticles." *Angew. Chem. Int. Ed,* 52: 12298-12302 that SPIONPs tagged NSCs could be effectively manipulated by the external spinning magnetic field for in situ NSC extraction. Besides the strong magnetization of the SPIONPs, it possesses high $r_2$ relaxivity for T2 weighted MR images. Nevertheless, its clinical application in imaging is limited. In addition to the aforementioned negative contrast effect, the magnetic susceptibility of SPIONPs contributes to the local field gradient artifacts, leading to poor resolution and distorted anatomy. Despite the unfavorable magnetic susceptibility artifacts for imaging, the magnetic moment generated in the presence of an external magnetic field is critical for levitating the NSCs. In the MRI device, radio frequency fields are essential to systematically vary the alignment of the magnetic moment. This would create a rotating magnetic field, which signalized the scanner for the construct of the detailed images. Taking the advantages of this activity, a magnetic agitation induced by this spinning magnetic field could be rendered to detach the magnetic labeled NSCs from V-SVZ with SPIONPs-based T2 contrast agent. MRI machine was no longer an imaging device but also a surgery tool for the in situ extraction of NSCs in a safe and practical manner. As shown in FIGS. 3a and 3b, the surface assessable-tagged NSCs of ependymal layer are significantly liberated from the V-SVZ when using T2 contrast agent right after the MRI scanning. On the contrary, no observable detachment of tagged stem cells could be seen with T1 contrast agent. It was worth noting that the animals were alive and apparently healthy even after receiving repeated MRI scanning. Consistent with the inventors' previous study, magnetic agitation is relatively safe and effective for the in situ NSCs harvest.

Figure 2C:
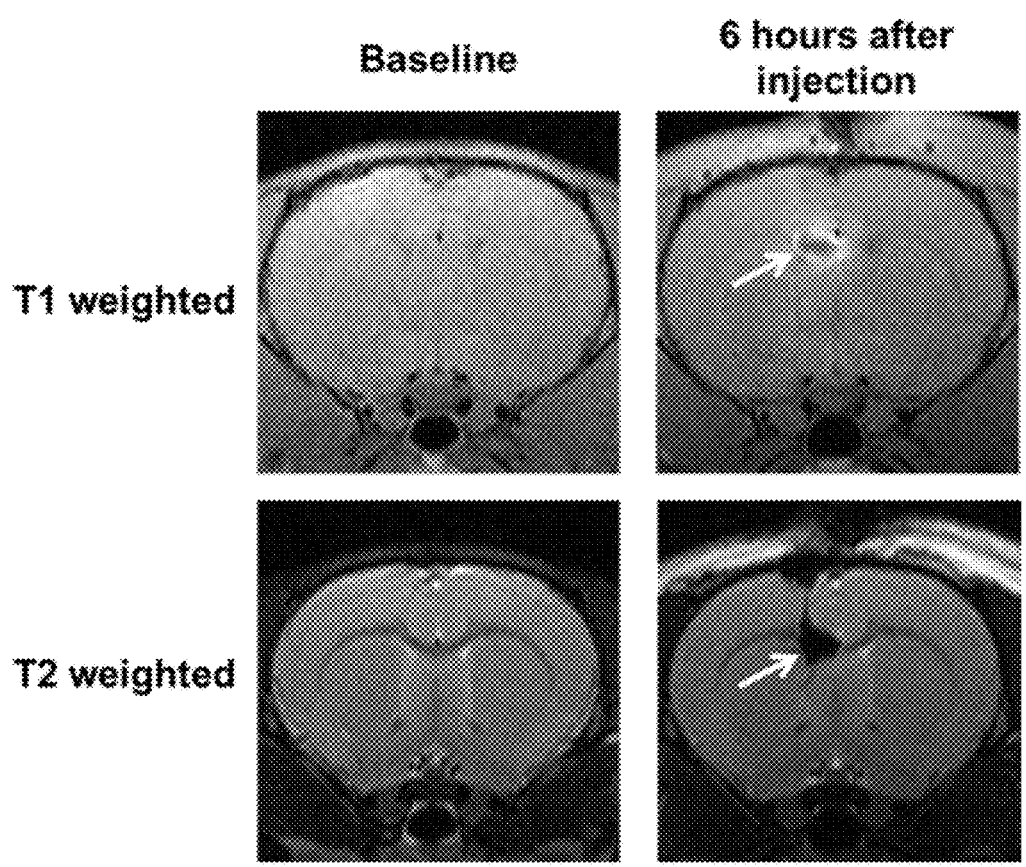
FIG. 2c shows in-situ T1/T2 contrast core-shell nanoparticles-stem cells from a rat subject. The contrast core-shell nanoparticles is dual-mode contrast agents (DMCA) of the present invention. The DMCA are unilaterally injected into the left V-SVZ for the tracking of the CD133$^+$ NSCs. After 6 hour-incubation, the CAs are able to specifically label the cells for the harvest. The DMCA can provide both T1 and T2 signals for visualizing the NSCs of V-SVZ. The arrow indicates the regions of interest.
Figure 2D:
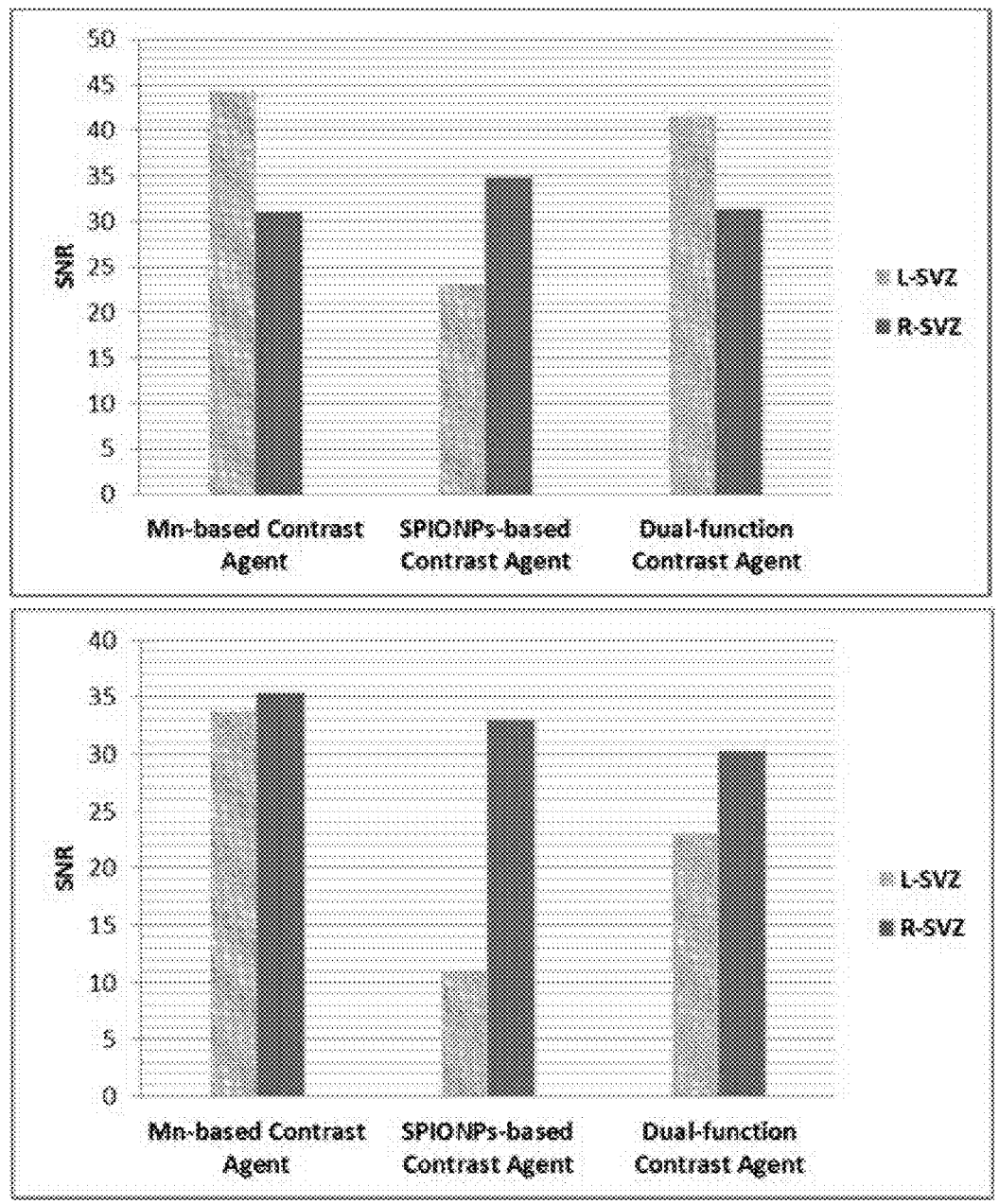
FIG. 2d shows a comparison of the T1-weighted signal (top) and the T2-weighted signal (bottom) amongst different contrast agents (CAs) on the selected area in rat brain.
Figure 3C:
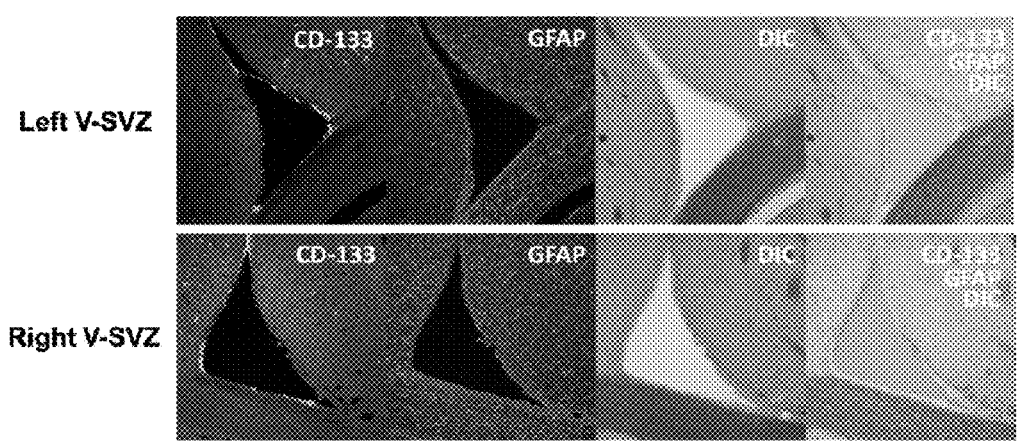
FIG. 3c shows the efficiency of neural stem cell detachment with T1/T2 contrast agent (DMCA) under the magnetic field from MRI machine. The CAs are unilaterally injected into the left V-SVZ. With the external magnetic field generated from the MRI, a magnetic agitation for the CD133$^+$ NSCs harvest can be performed. An effective detachment of the NSCs from the choroid plexus lining along the V-SVZ can be noticed with the DMCA and no severe damages can be observed with the DMCA, revealing that DMCA can serve as a safe and effective surgical tool for both diagnostic imaging and NSCs harvest in real time.
Figure 4A:
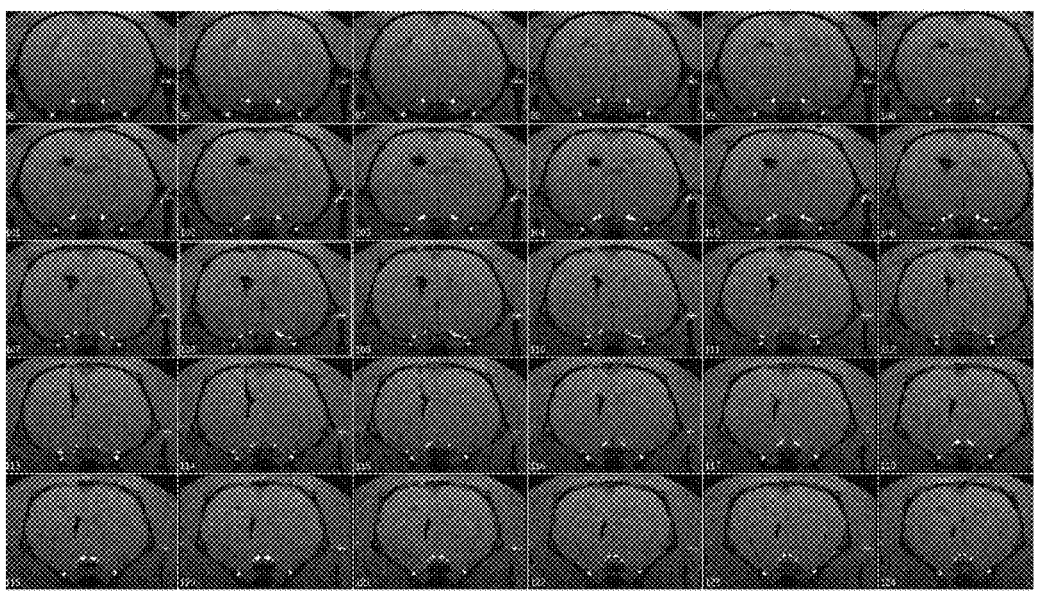
FIG. 4a shows a spatial distribution of T1-weighted MR imaging in a rat brain with T1/T2 dual-mode contrast agent. The highest contrast is confined only to the ventricular surface of V-SVZ DMCA.
Figure 4B:
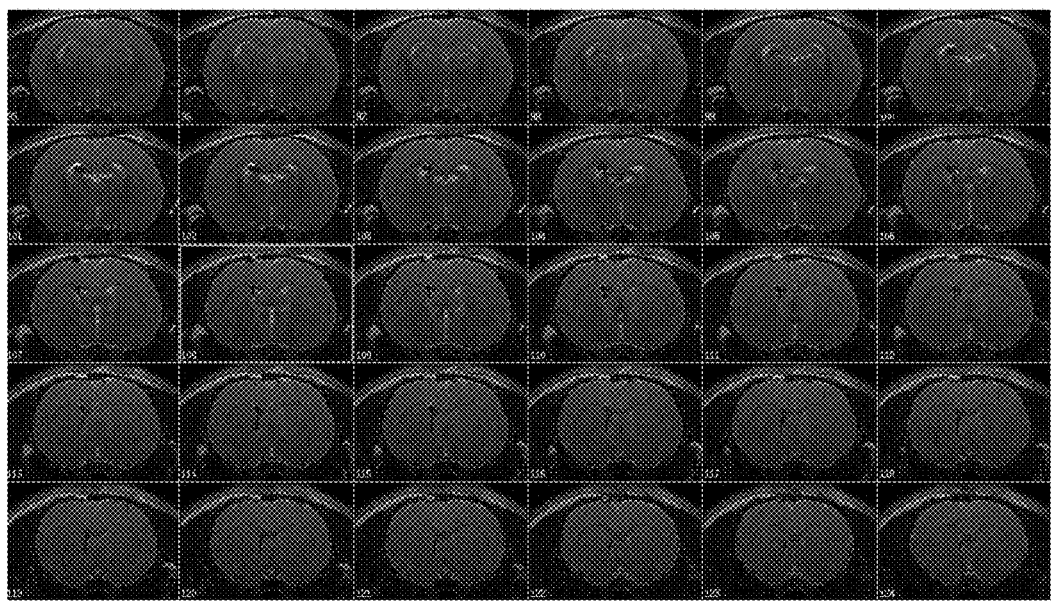
FIG. 4b shows a spatial distribution of T2-weighted MR imaging in a rat brain with T1/T2 dual-mode contrast agent. The highest contrast is confined only to the ventricular surface of V-SVZ DMCA.
Figure 5:
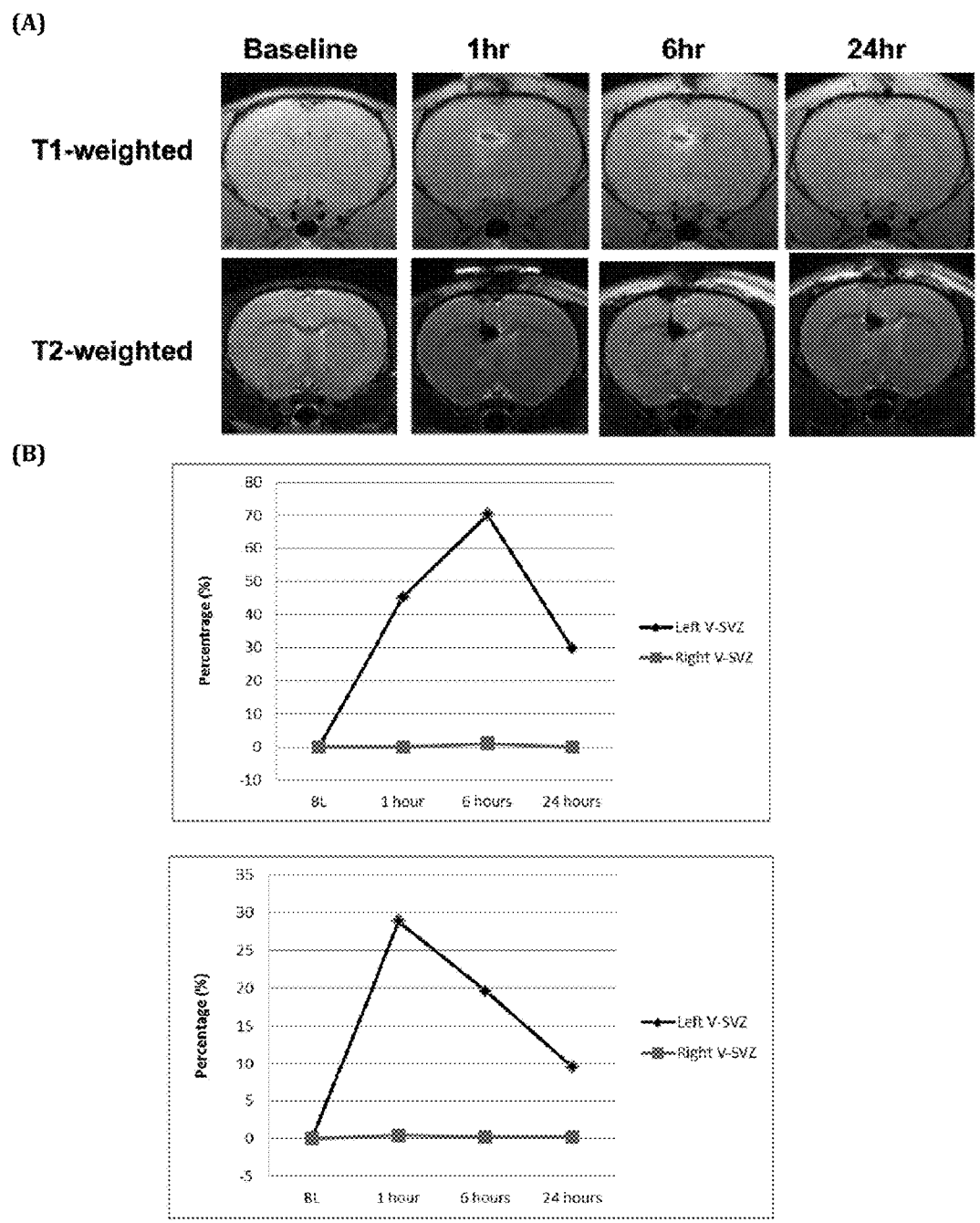
FIG. 5 shows a time course T1-T2 signals of the regions of interest in rat brain at different time intervals (1 hour, 6 hours and 24 hours): (A) A series of T1-weighted and T2-weighted images of labeled NSCs from the choroid plexus lining along the V-SVZ after the injection of DMCA; (B) The diagrams illustrate a significant drop of the T1 (left) and T2 (right) signals are observed after 24 hours.
Figure 6:
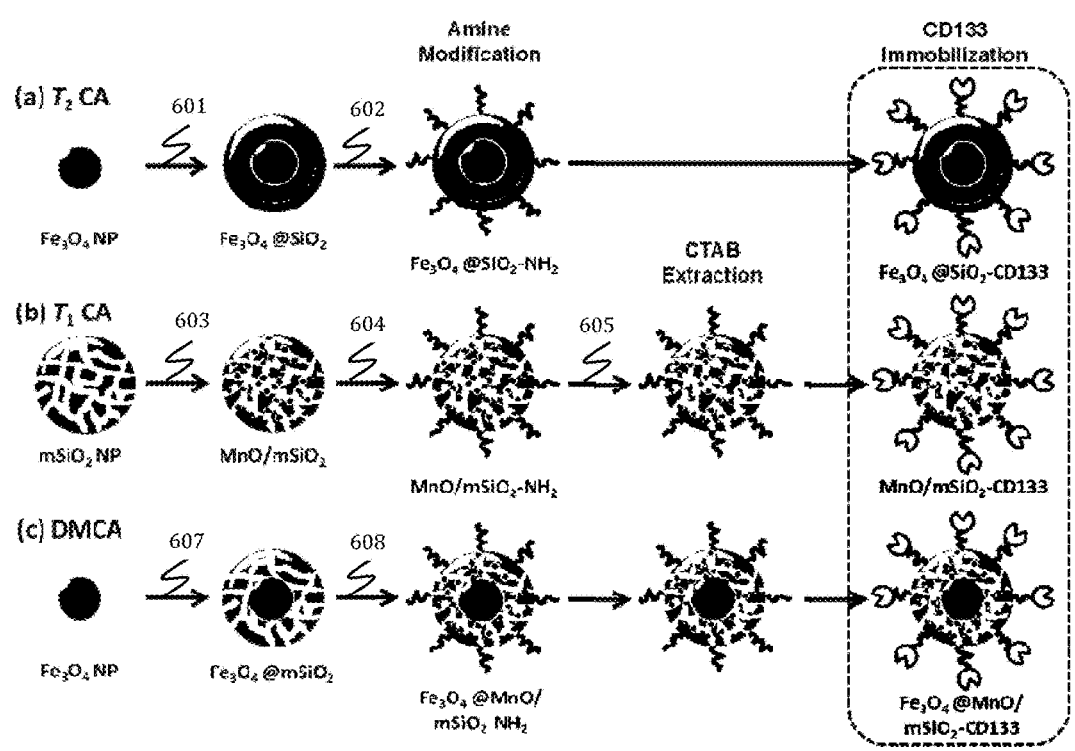
FIG. 6 shows Scheme 1: Schematic illustration of the synthesis of $Fe_3O_4$@MnO/$mSiO_2$-CD133 nanocomposites.

Considering the great challenges in real-time monitoring the in situ stem cell extraction, a new strategy towards the development of a dual-function contrast agent with both T1 and T2 modalities is pivotal. However, simply adding T1 materials by physical mixing or diluting T2 are ineffective to improve the image quality. The method of the present invention therefore comprises placing superfine T1 species, MnO, in the porous silica shell which can greatly attenuate the T2 effect from encapsulated magnetic nanoparticle at the core of the nanoparticle due to their close proximity (FIG. 6). On the other hand, the T1 effect can still be monitored without affecting the magnetic moment of T2 (FIG. 2c). Besides, the clearance of the particles could be observed 24 hours after the injection (FIG. 5). The drop of the CNS signals indicates the low risk of the accumulation, which might evoke unwanted health problems. As seen from the in situ experiments (FIG. 2c), both T1 (bright spot) and T2 (dark spots) with stable signal to noise ratios are clearly evident in the V-SVZ of a living rat at good resolutions. Simultaneously, magnetic agitation could be easily undergone to detach the tagged NSCs with this new dual-function contrast agent under the magnetic field from MRI machine (FIG. 3c). It is further demonstrated that the contrast agents of the present invention could offer a more feasible isolation of NSCs from other cells in the brain than other contrast agents. As shown in FIG. 3c, the detached cells are apparently intact and capable of sustaining the strong magnetic field during the MRI scanning. Unlike the dual-function contrast agent, more damages to the cells could be obviously found if using T2 material solely (FIG. 3b). It is suggested that the reciprocal relationship of $r_1$ and $r_2$, which are both comparable in the case of this novel contrast agent, could diminish and optimize the magnetization effect of the dual-function contrast agent for a safe and effective isolation of NSCs from the ependymal layer. In a high-resolution MRI scanning, a spatial distribution of the injected the dual-function contrast agent could be clearly revealed (FIG. 4). The highest contrast was confined only to the ventricular surface of V-SVZ, indicating that the contrast agent could preferentially bind to the ependyma. No detectable signals are shown in the ventricular lumen of V-SVZ or other brain areas. It is anticipated that this new nanomaterial could enable dual mode of using T1 and T2 imaging to give highly accurate information. The tomographic MRI images of tagged stem cells and their responses to external magnetic field could also offer new diagnostic information leading to breakthrough in neural stem cells study for in situ MRI imaging and magnetic isolation of stem cells.

No doubt that the nanoparticles of the present invention configured for both magnetic separation as well as contrast agents, which could offer for the first time, provide a simple and feasible NSCs harvest for patients who need an individual personalized therapy alternative to the conventional therapy, e.g., a regenerative medicine from a multipotent/pluripotent cell source of the patients themselves. The present invention also embarks on a new direction in the utility of the MRI machine as a surgery tool in combination with the use of the contrast agents of the present invention. In addition to the great T1 and T2 relaxivities of this new material for the accurate and comprehensive reconstruction of the NSC distribution, the inventors can effortlessly levitate the magnetic tagged NSCs from the ependymal layers of SVZ/LV with the magnetic field generated from the MRI machine. Taking together the novel advancement in the dual-functional materials and the different clinical applications of the MRI machine, the present invention fully demonstrates the possibility to simultaneously trace the stem cells locations and monitor the extraction in one single and non-invasive procedure. This technique represents an important first step in the individualized cell replacement therapy—treating the patients themselves by their own neural stem cells without the consideration of ethical issues and immune rejection.

Methods:

Synthesis of the T1-T2 Dual-Mode Contrast Agent

A new T1-T2 dual-mode contrast agent (DMCA) has been strategically designed and synthesized. Silica has been widely applied in biomaterial applications as it protects nanoparticles (NPs) from the external environment and it can be functionalized easily. Thus, the present invention provides a hollow mesoporous silica which possesses three distinct topological domains that can be independently functionalized: (1) the hollow interior core, (2) the worm-like nanochannels, and (3) the silica outmost surface. In an embodiment, the interior core can be made of iron oxide. To avoid the perturbation from direct contact of T1 and T2 CAs, the hollow core and the worm-like nanochannels are functionalized separately to form a T2 CA ($Fe_3O_4$ NP) and a T1 CA (MnO NPs). Moreover, such a structural design not only increases water accessibility of MnO NPs but also provides mechanical resistance against clustering (harmful to T1-weighted imaging) under physiological conditions. The outmost silica surface of the designed product, $Fe_3O_4$@MnO/$mSiO_2$, is further immobilized anti-CD133 antibodies for specific targeting. The in vivo result described herein demonstrates that $Fe_3O_4$@MnO/$mSiO_2$-CD133 NPs could be a potential platform for neural stem cell extraction and T1-T2 dual-modal MRI monitoring.

Animal Used

Adult Sprague-Dawley (SD) rats weighing 200-220 g were employed in the experiments. The animal experimental protocols performed in this study strictly confirmed and approved by the guidelines of the Animals (Control of Experiments) Ordinance, Department of Health, Hong Kong, the Committee on the Use of Human and Animal Subjects in Teaching and Research, Hong Kong Baptist University, and the Principles of Laboratory Animal Care (NIH publication no. 86-23, revised 1985). Both number and suffering of the animals were aimed to minimize in all procedures.

In Vivo MRI Experiments

The details of the micro-surgery could be found in the previous study in Lui C. N. P., Tsui Y. P., Ho A. S. L., Shum D. K. Y, Chan Y. S., Wu C. T., Li H. W., Tsang S. C. E. and Yung K. K. L. (2013). "Neural Stem Cells Harvested from Live Brains by Antibody-Conjugated Magnetic Nanoparticles." *Angew. Chem. Int. Ed*, 52: 12298-12302, where the disclosure of which is incorporated herein by reference in its entirety. For in vivo MRI experiments, all animals are anesthetized with 5% isoflurane at 1-1.5 L min-1 airflow. The images would be captured with a Biospec 4.7 T spectrometer (Bruker) before and at different times after the injection of several contrast agents with (T1/T2): $T_R$=600/4500 ms, (T1/T2) $TE_{eff}$=10.1/70 ms, FOV=30 mm×30 mm, slice thickness=0.8 mm, and matrix size=256×256 with six repetitions, where $T_R$ refers to repetition time; $TE_{eff}$ refers to effective echo time.

Perfusion

The rat is first deeply anesthetized with an overdose of sodium pentobarbital (60 mg/kg, i.p., Saggittal). It is then perfused transcardially with 250 ml of 0.9% saline to remove any blood followed by 250 ml fixative (3% paraformaldehyde with 0.1% glutaraldehyde solution in 0.1 M phosphate buffer (PB), pH 7.4) by using peristaltic pump. The perfusion flow rate is set to 25 ml/min for saline and 15 ml/min for fixative. The fixed brain is removed from the skull and stored overnight at 4° C. in post-fix solution (3% paraformaldehyde in 0.1 M PB, pH 7.4). The brain is rinsed three times with phosphate-buffered saline (PBS; 0.01 M, pH 7.4) and then cut into 70 μm sections by using vibratome. All the sections are collected in PBS at 4° C. before use. Immunofluorescence is performed to illustrate the immunoreactivity for CD133 and Glial fibrillary acidic protein (GFAP). Furthermore, the extracted cells are also mounted on clean slides with mounting medium (Dako) and covered with coverslips for the examination under the same parameters with laser scan confocal microscope (Olympus fluoview 1000).

Statistical Analysis

Mean±SD or SEM are indicated in the figures. Student's t-test is used to calculate the p-value between the experimental group and the control group. p-values<0.5 are considered significant.

Further Experiments

To achieve both accurate real-time monitoring and harvesting of NSCs, in one embodiment of the present invention, it is strategically designed a novel DMCA comprising an iron oxide core and a functionalized mesoporous shell ($Fe_3O_4$@MnO/$mSiO_2$-CD133, where ultrasmall MnO NPs are dispersed within mesopores and CD133 is an antibody modified on outmost surface of particle). In one embodiment, the average size of the ultrasmall MnO NPs is about 2.5 nm. In another embodiment, the average size of the mesopore with the silica coating is about 19.5 nm. The $Fe_3O_4$ core serves not only as magnet for magnetic cell collection but also provides the capability for T2-weighted MRI. The mesoporous framework of silica not only provides a template for the synthesis of ultrasmall MnO NPs but also increases water permeability to those T1 CAs. The silica framework also avoids the direct contact of T1 and T2 CAs and thus the perturbation of T1 relaxation from the magnetic field generated by $Fe_3O_4$ NP is suppressed (vide infra). Both of each greatly enhance the r1 relaxivity. The leakage and clustering of ultrasmall MnO NPs (decrease T1 contrast) under physiological conditions can be minimized by mechanical resistance provided by the silica template. The anti-CD133 antibodies anchored on outmost surface is for targeting neural stem cells. The amine group (for CD133 immobilization) can also be easily and specifically modified on outmost silica surface without penetration into mesopores, avoiding decrease of $r_1$ relaxivity. Also, systematically investigation on the cell/host damage caused versus T1, T2 and DMCA during MR measurement has, for the first time, been studied. Most importantly, the serious damage to both cell and host caused by T2 CA could be greatly reduced when T1 CAs are introduced (vide infra). Finally, the DMCA (i.e. $Fe_3O_4$@MnO/m$SiO_2$-CD133) is demonstrated to be a promising candidate for dual-mode cell tracking and no observable damages to both cell and host during cell collection.

Manganese (Mn) has been recently received special attention as versatile T1 positive Scheme a (FIG. 6) illustrates the overall synthetic protocol (detail of the synthesis is described in the experimental section) of T2 ($Fe_3O_4$@$SiO_2$-CD133), T1 (MnO/m$SiO_2$-CD133) and DMCA ($Fe_3O_4$@MnO/m$SiO_2$-CD133). For the preparation of $Fe_3O_4$@$SiO_2$-CD133 (FIG. 6: Scheme a), the core iron oxide NPs are synthesized first by the thermal decomposition of Fe(acac)$_3$ precursor in octadecene. (TEM & XRD) Silica shell is then coated to the as-prepared $Fe_3O_4$ NP with a sol-gel reaction of tetraethyl orthosilicate (TEOS) via a reverse micro-emulsion method. (TEM & XRD & EDX) (601). To conjugate targeting molecules (i.e. antibody CD133) on silica surface, the resulting product, $Fe_3O_4$@$SiO_2$ NPs, are then further modified with (3-aminopropyl)triethoxysilane (APTMS) under basic condition (602) to yield $Fe_3O_4$@$SiO_2$—$NH_2$. Since the hydroxyl groups are negatively charged at neutral pH (Si—$O^-$), the modification of amine group (positive charged in neutral pH, $NH_3^+$) is identified with zeta potential (ζ-potential) measurement. The value of ζ-potential for $Fe_3O_4$@$SiO_2$ increases positively from −44 mV to −19 mV after APTMS modification, suggesting the successful replacement of surface hydroxyl groups by amine groups. Anti-CD133 antibodies can then be conjugated to $Fe_3O_4$@$SiO_2$—$NH_2$ via an amide bond formation between the amine and the carboxylic acid of CD133. The successful immobilization of CD133 on $Fe_3O_4$@$SiO_2$ can be identified with the Fourier Transform Infra-Red (FT-IR).

Since the spin-lattice relaxation can be greatly accelerated by direct contact between water proton and T1 CA, high water accessibility to T1 CA and high surface area of T1 CA have been regarded as two critical concerns for the design of new nanoparticle-based T1 CA. Even though the high surface to volume ratio can be achieved easily by introduction of ultrasmall size particle, the strongly coordinating surfactants should be applied to prevent clustering of particles, which would result in intensive T2 contrast increase and hence disappearance of T1, under physiological conditions. However, the strong coordination minimizes the number of coordinated water molecules (q) to a paramagnetic center, hence the reduction of inner-sphere relaxivity ($r_1^{IS}$) and overall longitudinal relaxivity ($r_1$). To address those difficulties, a post-synthesis strategy is employed (FIG. 6: Scheme b) that T1 CAs (MnO NPs) can be homogeneously dispersed in the mesoporous silica (m$SiO_2$) framework. Such a structural design not only makes MnO NPs inside the m$SiO_2$ framework free from surfactant coordination (increase parameter q of $r_1^{IS}$) but also provides mechanical resistance against clustering under physiological conditions. More importantly, the average pore size of m$SiO_2$ is ~2.5 nm, which matches well the diameter of the NPs to be synthesized inside as well as to greatly enhance the overall surface area of MnO NPs. The m$SiO_2$ NPs are prepared according to a previously reported procedure in Lui et al. (2013) and a brief synthetic route is elaborated in the experimental section. The as-prepared m$SiO_2$ NPs (FIG. 6, scheme b) are added to the mixed solution of manganese chloride ($MnCl_2$) and triethylene glycol (603). MnO NPs embedded in m$SiO_2$ (MnO/m$SiO_2$) are obtained by raising temperature to 200° C. and kept at that temperature for 6 hours. (TEM & XRD & EDX) Following the amine modification (604), the CTAB templates are then removed via an ion exchange method (see examples described herein) (605), leaving the void of nanopores, which increases water permeability to the embedded MnO NPs for T1 signal. (TGA) It should be noted here that the amine modification should be carried out before the CTAB extraction. According to previous embodiments of the present invention, the $r_1$ value would decrease if CTAB is extracted before amine modification. Such a step makes silanols more easily functionalized on the surface of embedded MnO NPs and thus hampered the accessibility of water from the surrounding environment. The final T1 CA, MnO/m$SiO_2$-CD133, is prepared via an amide bond formation between the amine of MnO/m$SiO_2$—$NH_2$ and the carboxylic acid of CD133.

For the preparation of DMCA ($Fe_3O_4$@MnO/m$SiO_2$-CD133) (FIG. 6: Scheme c), the procedure is similar to MnO/m$SiO_2$-CD133 but using $Fe_3O_4$@m$SiO_2$ instead of m$SiO_2$ as template to grow MnO NPs. Synthetic details of coating mesoporous shell on $Fe_3O_4$ core ($Fe_3O_4$@m$SiO_2$) is elaborated in the example section. Briefly, first of all, hydrophobic $Fe_3O_4$ NPs are transferred to the aqueous phase by utilizing cetyltrimethylammonium bromide (CTAB) (607). In the subsequent sol-gel reaction, CTAB-stabilized $Fe_3O_4$NPs act as seeds for the formation of spherical mesoporous silica shells by hydrolysis and condensation of TEOS. Herein, CTAB serves as not only the secondary stabilizer for the transfer of the $Fe_3O_4$ NPs to the aqueous phase but also the organic templates for the formation of the mesoporous silica shells. In this core/shell structure, the silica-CTAB layer is formed locally around the CTAB-$Fe_3O_4$ NPs under basic conditions through an electrostatic interaction between the cationic (CTAB) and anionic (silicate) species. The corresponding TEM images of $Fe_3O_4$@m$SiO_2$ and $Fe_3O_4$@MnO/m$SiO_2$ are shown in FIG. 1 respectively. (TEM & XRD & EDX). Once the silica outmost surface is formed, amine functionalization can be performed thereon for conjugation with antibodies which require $NH_2$ (608).

T1/T2 dual contrast agents can be obtained by combining T1 and T2 contrast materials, until now, a rational design concept of dual mode MRI contrast agents has not been proposed. For example, Bae et al. and Yang et al. in K. H. Bae, Y. B. Kim, Y. Lee, J. Hwang, H. Park, T. G. Park, *Bioconjugate Chem.* 2010, 21, 505-512 and H. Yang, Y. Zhuang, Y. Sun, A. Dai, X. Shi, D. Wu, F. Li, H. Hu, S. Yang, *Biomaterials* 2011, 32, 4584-4593, where the disclosure of which is incorporated herein by reference in its entirety, recently synthesized T1/T2 dual CAs through modifying Gd-DTPA molecules on the surface of magnetic iron oxide nanoparticles. The main problem for these systems, in which T1 and T2 CAs contact directly, is that the magnetic field generated by a superparamagnetic T2 CA perturbs the relaxation process of the paramagnetic T1 CA. To separate T2 and T1 material in a single unit, Cheon's group in J.-S. Choi, J.-H. Lee, T-H. Shin, H.-T. Song, E. Y. Kim, J. Cheon, *J. Am. Chem. Soc.* 2010, 132, 11015-11017, where the disclosure of which is incorporated herein by reference in its entirety, developed a core-shell-shell structure, $MnFe_2O_4$@$SiO_2$@$Gd_2O(CO_3)_2$, in which the T2 CA ($MnFe_2O_4$) and $T_1$ CA ($Gd_2O(CO_3)_2$) were separated by a $SiO_2$ layer with tunable thickness. They showed that the quenching of the T1 signal by the T2 superparamagnetic core dramatically decreases from 94% to 0% by increasing the thickness of the separating layer to 16 nm. However, all Gd-based T1 CA are hazardous once if they dissociate and accumulate in the body and are also associated with life-threatening nephrogenic systemic fibrosis. Compared with $Gd^{3+}$, $Mn^{2+}$ is much less toxic and has been shown to exhibit comparable in vivo $r_1$ MR relaxivities. Even though, very recently, Im et al. in G. H. Im, S. M. Kim, D. G. Lee, W. J. Lee, J. H. Lee, I. S. Lee, *Biomaterials* 2013, 34, 2069-2076, where the disclosure of which is incorporated herein by reference in its entirety, introduced the $Fe_3O_4$/MnO dumbbell-shaped nanocrystal that provides a negative T2 contrast effect when the nanocrystal is intact, the T1 contrast appears only when the $Mn^{2+}$ ions are released in a low pH environment. Moreover, the above-mentioned DMCAs require sophisticated and elaborate ligand design to anchor NPs for additional functionalities such as specific targeting, optical imaging, biocompatible and drug delivery properties. Syntheses of these multifunctionalized ligands, however, are nontrivial, cost demanding, and may not be applicable for large-scale production.

To address those difficulties, one embodiment of the present invention provides hollow mesoporous silica as the framework of the newly developed DMCA in the present invention since silica is a material with high biocompatibility and is also much easier to conjugate end-labeled silane molecules via the facile sol-gel chemistry. Most importantly, the hollow mesoporous structure of the present invention provides three parts (hollow interior, worm-like nanochannels and outmost surface) that can be functionalized and utilized independently. The as-prepared DMCA, $Fe_3O_4$@MnO/m$SiO_2$-CD133, comprises a $Fe_3O_4$ NP in the hollow interior and a mesoporous shell with ultrasmall MnO NPs dispersed within mesopores (or defined herein as worm-like nanochannels) and antibodies (CD133) modified specifically on outmost surface. Such a design provides several advantages summarized as follow: (1) The silica framework avoids the direct contact of T1 and T2 CAs and thus the perturbation of T1 relaxation from the magnetic field generated by $Fe_3O_4$ NP can be suppressed. (2) The mesopore not only makes synthesis of ultrasmall MnO NPs (without surfactant) feasible but also increases water accessibility to MnO NPs. Both of each greatly enhance the $r_1$ relaxivity. (3) The leakage and clustering of ultrasmall MnO NPs (decrease T1 contrast) under physiological conditions can be minimized by mechanical resistance provided by silica template. (4) The amine group (for CD133 immobilization) can be easily and specifically modified on outmost silica surface without penetration into mesopores, avoiding decrease of $r_1$ relaxivity.

In one embodiment of the present invention, each of T1 CA, T2 CA and DMCA (2000 ug mL$^{-1}$ in 5 mL of PBS) is unilaterally injected into the V-SVZ of the animals (FIG. 2a-c) to compare the contrast effect among the three CAs and the sensitivity of the traditional CAs with the DMCA of the present invention. With the anti-CD133 antibodies tagged on the CAs, all of the CAs of the present invention could specifically localize to NSCs of V-SVZ linings and no dispersal of the nanoparticles could be observed in the brain. The spatial distribution of the nanoparticles is monitored for 6 hours after the injection where extensive binding of the nanoparticles to the NSCs has been shown in previous study in Lui et al, (2013). In agreement with the literature, a positive contrast can be noticed in the T1-weighted MRI but not in the T2-weighted MRI with the Mn-based contrast agent [FIG. 2a]. A clear and bright image with outstanding accuracy can be revealed by T1 CA. As expected, T2 CA would have dark effect on MRI [FIG. 2b]. In addition to the negative contrast, the magnetic susceptibility of T2 CA contributes to the local field gradient artifacts, leading to poor resolution and distorted anatomy. Its clinical application in imaging is limited. There is no doubt that using T1 CA can avoid the mis-interpretation of the MRI images due to the negative contrast which often confuse with the low-level MRI signal from adjacent tissues, including bone or vasculature of brain. As concerning that V-SVZ is located in close proximity to blood vessel scaffold, the $T_1$ contrast agent can eliminate this drawback and satisfy the need for an effective labeling and accurate tracking of NSCs.

Despite the unfavourable magnetic susceptibility artifacts for imaging, the strong magnetic moment of $T_2$ CA generated in the presence of an external magnetic field is critical for levitating the NSCs. One embodiment of the present invention has demonstrated that SPIONPs tagged NSCs can be effectively manipulated by the external spinning magnetic field for in situ NSC extraction. In the MRI device, radio frequency fields are essential to systematically vary the alignment of the magnetic moment. This would create a change in magnetic field which signalize the scanner for the construct of the detailed images. Taking the advantages of the magnetic field generated from the MRI, a magnetic agitation would induce and render the detachment of the magnetic labeled NSCs from V-SVZ with T2 contrast agent. MRI device is no longer just an imaging device but also a surgery tool for the in situ extraction of NSCs in a safe and practical manner. As shown in FIGS. 3a and 3b, the surface assessable tagged NSCs of ependymal layer are significantly liberated from the V-SVZ when using $T_2$ CA after the MRI scanning. In the contrary, no observable detachment of tagged stem cells can be seen with T1 contrast agent. It is worth noting that the animals are still alive and apparently healthy even after receiving repeated MRI scanning. Consistent with previous embodiments of the present invention, magnetic agitation is relatively safe and effective for the in situ NSCs harvest.

Considering the great challenges in real-time monitoring the in situ stem cell extraction, a new strategy towards the development of a dual-function contrast agent with both T1 and T2 modalities is pivotal. However, simply adding T1 materials by physical mixing or diluting T2 are ineffective to improve the image quality. In one embodiment of the present invention, strategically-designed DMCA can overcome the shortcomings of the traditional CAs. The DMCA of the present invention can enable another objective of the present invention to analyze the tomographic images of tagged NSCs and monitor the harvest of the NSCs in the subject's brain alive with a high spatial and temporal resolution in real time. As seen from the in situ experiments [FIG. 2c] both T1-weighted image (bright spot) and T2-weighted image (dark spots) with stable signal-to-noise ratios are clearly evident in the V-SVZ of a living rat at good resolutions. In the meantime, magnetic agitation can be effortlessly undergone to detach the magnetic tagged NSCs with this new dual-function CA under the magnetic field from MRI machine [FIG. 3c]. Notably, the detached cells are apparently intact and capable of sustaining the strong magnetic field during the MRI scanning with DMCA while more damages to the cells can be obviously shown with T2 material solely (FIG. 3b). It is suggested that the reciprocal relationship of $r_1$ and $r_2$ could balance and optimize the magnetization effect of the DMCA for a safe and effective isolation of NSCs from the ependymal layer. In a high-resolution MRI scanning, a spatial distribution of the injected DMCA could be clearly revealed [FIG. 4]. The highest contrast is confined only to the ventricular surface of V-SVZ, indicating that the contrast agent can preferentially bind to the ependyma. No detectable signals are shown in the ventricular lumen of V-SVZ or other brain areas. It is anticipated that the DMCA of the present invention can enable dual mode of using T1 and T2 imaging to give highly accurate information. The tomographic MRI images of tagged stem cells and their responses to external magnetic field can also offer new diagnostic information, leading to breakthrough in the field of in situ MRI imaging and magnetic isolation of stem cells, especially neural stem cells.

Figure 7:
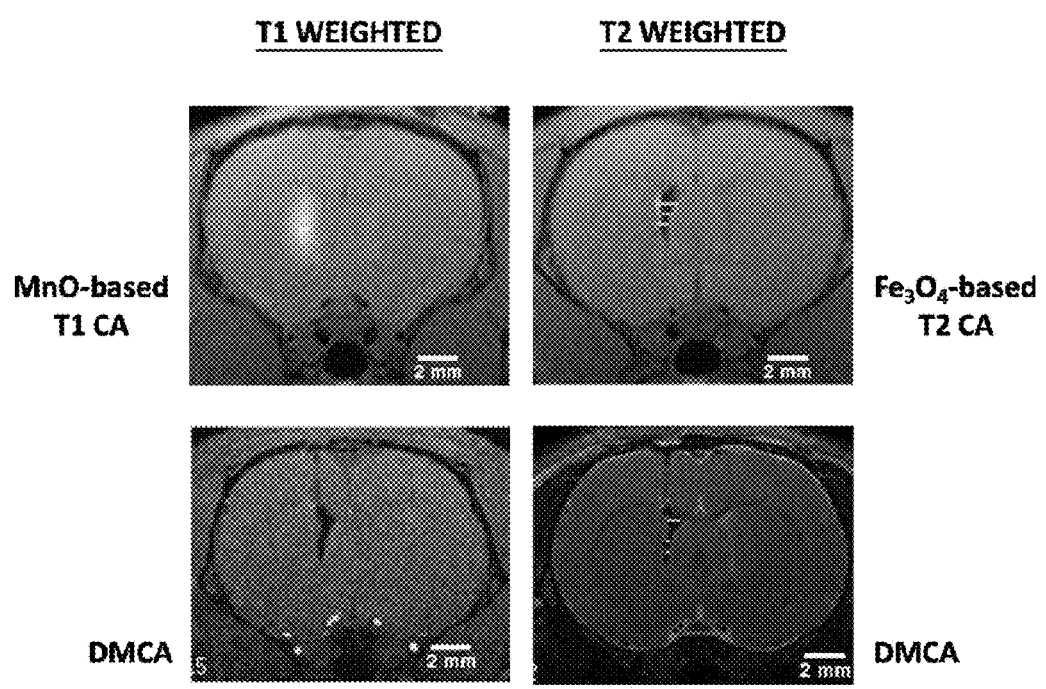
FIG. 7 shows the result of MRI signal intensity of the labeled NSCs. DMCA can amplify the signal to an observable level without further creating the artifacts like MnO-based T1 CA and $Fe_3O_4$-based T2 CA. DMCA can increase the accuracy of the anatomical information from the MRI images. A single-cell MRI study would be achieved.
Figure 8:
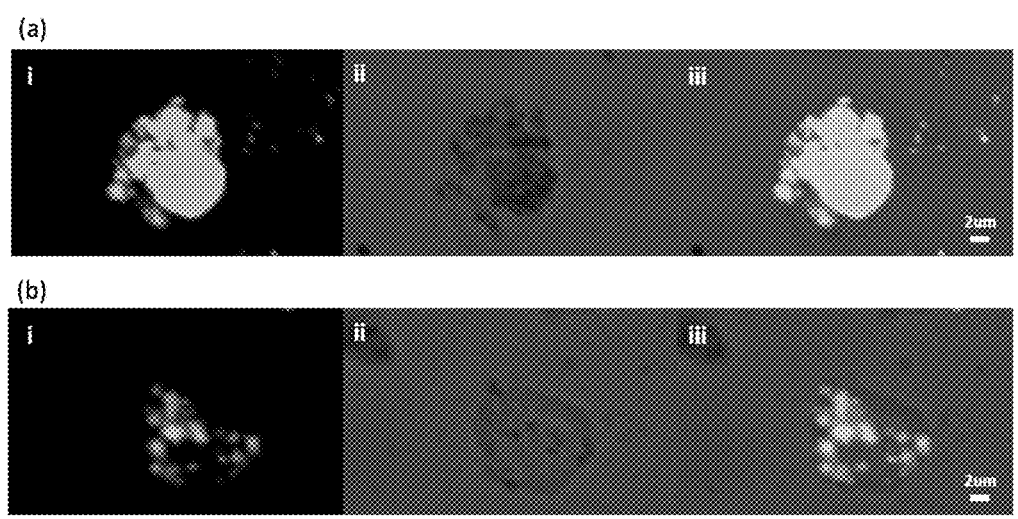
FIG. 8 shows the internalization of the nanoparticles. Confocal microscopic examination of the localization of DMCA on the NSCs was performed. The detached NSCs are collected (a) 6 hours after the injection and (b) 24 hours after the injection, respectively. Fewer particles are bound on the cells and the uptake of the DMCA is observed after 24 hours.

One embodiment of the present invention has also demonstrated the in situ single-cell MRI scanning of NSCs in a living subject. The cells of interest can be precisely located and identified for the surgical navigation under MRI. As proposed by several literatures [F. Doetsch, J. M. Garcia-Verdugo, A. Alvarez-Buylla, Cellular composition and three-dimensional organization of the subventricular germinal zone in the adult mammalian brain. The Journal of neuroscience: the official journal of the Society for Neuroscience 17, 5046 (Jul. 1, 1997); C. Lee et al., The molecular profiles of neural stem cell niche in the adult subventricular zone. PloS one 7, e50501 (2012); M. W. Brightman, S. L. Palay, The Fine Structure of Ependyma in the Brain of the Rat. The Journal of cell biology 19, 415 (November, 1963)], the diameter of the ependymal cells was ranged from 1 to 2 cell layers (0.015-0.050 mm) which was hard to accurately observe in the MRI. The present embodiment is able to amplify the signal to a certain level without further creating the artifacts. The DMCA according to that embodiment of the present invention allows an improved detection of the cells and visualizes them up to 0.195±0.020 mm under T1-weighted imaging [FIG. 7]. Significant and useful information can be retained. However, with the traditional T1 CA and T2 CA, the thickness of the ependymal layer is reflected as 0.320±0.046 mm and 0.378±0.052 mm, respectively [FIG. 7]. This kind of information obtained from using traditional CAs would provide an incorrect anatomical data for coordinating and collecting of the detached NSCs from the V-SVZ. Besides, the clearance of the nanoparticles of the present invention can be observed 24 hours after the injection [FIGS. 12 and 13]. The drop of the CNS signals indicated the low risk of the accumulation which might evoke unwanted health problems.

Figure 9:
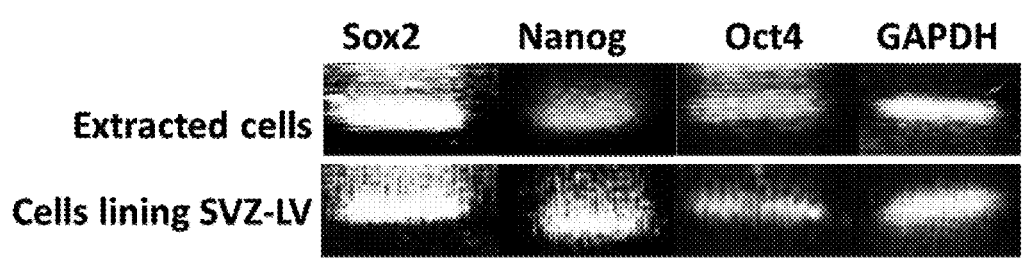
FIG. 9 shows gene expression analysis using semi-quantitative RT-PCR. The key transcription factors (Sox2, Nanog and Oct4) for stem cell identity are expressed in both the dissected V-SVZ tissue and the DMCA tagged cells.

To address whether the extracted cells possess the stemness, in some embodiments of the present invention, the cells extracted according to the method of the present invention are cultured to neurospheres and differentiated them into different phenotypes. Other embodiments of the present invention further elucidate the potency of the extracted cells. Sox2, Nanog and Oct4 are well-considered as the key transcription factors for maintaining the stem cell identity. Given the notion that the expression of these defined transcription factors can regulate the signaling pathways on self-renewal and proliferation for pluripotent phenotype, the ependymal tissue is collected from the walls of V-SVZ by dissection to compare the gene expressions of those transcription factors for self-renewal and proliferation of the pluripotent phenotype in ependymal tissue with the ones in the extracted cells. As expected, RT-PCR analysis reveals that both of the dissected ependyma and the extracted cells exhibit the endogenous stem cell markers (FIG. 9).

No doubt that the exciting developments of tailored nanoparticles of the present invention for both magnetic separation as well as contrast agents, which could offer for the first time, provide a simple and feasible NSC harvest for patients in needs of cell source for regenerative medicine. Another embodiment of the present invention also embarks on a new direction in the utility of the MRI machine as a surgery tool in combination with the use of the contrast agents of the present invention. In addition to the great T1 and T2 relaxivities of this new material for the accurate and comprehensive reconstruction of the NSC distribution, the present invention can effortlessly levitate the magnetic tagged NSCs from the ependymal layers of V-SVZ with the magnetic field generated from the MRI machine. Taking together the novel advancement in the DMCA of the present invention and the different clinical applications of the MRI machine according to an embodiment of the present invention, the present invention can fully demonstrate the possibility to simultaneously trace the stem cells locations and monitor the extraction in one single and non-invasive procedure. This technique represents an important first step in the individualized cell replacement therapy—treating the patients themselves by their own neural stem cells without the consideration of ethical issues and immune rejection.

EXAMPLES

Methodology:
Chemicals
Synthesis of Mesoporous Silica NPs (mSiO$_2$)
364 mg of CTAB was dissolved in 100 mL DI water (80° C.) under intensive stirring and light-sealed environment. After a clear solution was obtained, 0.83 mL of TEOS (tetraethyl orthosilicate) was added dropwise for 20 minutes. Immediately, 148 mg of NH4F which was used as a catalyzer for accelerating the hydrolyzation and condensation of silicon sources was added. After 1 hour, nanoparticles were collected and washed with ethanol and deionized water three times. Finally, products were dispersed in deionized water.

Synthesis of MnO/mSiO$_2$
The as-prepared mSiO$_2$ nanoparticles (see above) were used as template for synthesis of ultrasmall MnO NPs. Typically, mSiO$_2$ NPs (30 mg), MnC$_2$.4H$_2$O (660 mg) and 10 mL of triethylene glycol were added to a 50 mL three-necked flask and the mixture was magnetically stirred at room temperature under N$_2$ gas flow. The mixture solution was degassed at 100° C. in order to remove any moisture and oxygen. The reaction temperature was raised to 200° C. and kept at that temperature for 6 hours before cooling to room temperature. The solvent, unreacted coating ligand, unreacted Mn(II), and Cl− ions were removed from the reaction solution by washing it with distilled water several times.

Synthesis of Fe$_3$O$_4$ NPs
Fe(acac)$_3$ (176.5 mg), 1,2-hexadecanediol (645 mg), oleic acid (0.5 mL), oleylamine (0.5 mL), and octadecene (10 mL) were mixed and magnetically stirred under a flow of nitrogen. The mixture was heated to 200° C. for 30 min and then, under a blanket of nitrogen, heated to reflux (~300° C.) for another 30 min. The black-brown mixture was cooled to room temperature by removing the heat source. Under ambient conditions, ethanol (40 mL) was added to the mixture, and a black material was precipitated and separated via centrifugation. The product, Fe$_3$O$_4$ nanoparticles, was redispersed into hexane for storage.

Synthesis of Fe$_3$O$_4$@SiO$_2$
Fe$_3$O$_4$@SiO$_2$ nanocomposites were prepared from reverse micelles using a previously reported procedure. The as-prepared Fe$_3$O$_4$ NPs (see above) were used as seeds for growth of the SiO$_2$ shell Briefly, Fe$_3$O$_4$ nanoparticles (2 mg) and 100 μL of TEOS were added to a heterogeneous solution containing cyclohexane (24 mL), hexanol (4.8 mL), Triton X-100 (6 mL), and water (1 mL). After 6 hours of stirring, NH$_4$OH (100 mL) was added to initiate the hydrolysis of TEOS. The reaction was allowed to continue for another 24 hours with stirring at room temperature. The product, Fe$_3$O$_4$@SiO$_2$, was well dispersed in ethanol and was further purified by centrifugation.

Synthesis of $Fe_3O_4$@MnO/$mSiO_2$

For coating mesoporous silica shell on $Fe_3O_4$ NP ($Fe_3O_4$@$mSiO_2$), first of all, two milliliters of the $Fe_3O_4$ solution (10 mg/ml chloroform) were mixed with 100 mg of cetyltrimethylammonium bromide (CTAB) and 20 ml of water. The mixture was stirred vigorously, and then the chloroform solvent was boiled off from the solution. The transparent $Fe_3O_4$/CTAB solution was added to a mixture of 29.5 mL of water, 200 mg CTAB and 0.5 mL of 0.8 M NaOH solution, and the mixture is heated. At approximately 60° C. under stirring, 0.5 mL of TEOS and 3 mL of ethyl acetate were loaded to the reaction solution in sequence. The solution stayed stirred for another 6 hours. To growth ultrasmall MnO NPs in the mesoporous silica shell of the as-synthesized $Fe_3O_4$@$mSiO_2$, the similar procedure was carried out as MnO/$mSiO_2$.

Amine Modification

In order to immobilize CD133 antibody on silica outmost surface, amine modification was firstly carried out on as-synthesized NPs (i.e. MnO/$mSiO_2$, $Fe_3O_4$@$SiO_2$ and $Fe_3O_4$@MnO/$mSiO_2$). Briefly, 3-amino-propyltrimethoxysilane (10 μL) was added to a mixture of ethanol (30 mL), DI water (6 mL), $NH_4OH$ (300 μL), and as-prepared particles (20 mg). After 24 hours, the sample was centrifuged and washed several times to remove the unreacted chemicals. The precipitate of particles (i.e. MnO/$mSiO_2$—$NH_2$, $Fe_3O_4$@$SiO_2$—$NH_2$ and $Fe_3O_4$@MnO/$mSiO_2$—$NH_2$) was then collected and redispersed in DI water.

Removal of CTAB Template

Template molecules (CTAB) of MnO/$mSiO_2$—$NH_2$ and $Fe_3O_4$@MnO/$mSiO_2$—$NH_2$ were removed via a fast and efficient ion exchange method. The NPs (MnO/$mSiO_2$—$NH_2$ and $Fe_3O_4$@MnO/$mSiO_2$—$NH_2$) are transferred to 50 mL of ethanol containing 0.3 g of $NH_4NO_3$ and kept at 60° C. for 2 hours. The extraction step was repeated twice to remove the surfactants. After 48 hours of dialysis, the product (without CTAB) was prepared and ready for use.

CD133 Immobilization

The anti-CD133 antibodies were covalently conjugated onto the amine-functionalized silica surface by EDC/NHS chemistry. Typically, amine-functionalized particles (i.e. MnO/$mSiO_2$—$NH_2$, $Fe_3O_4$@$SiO_2$—$NH_2$ and $Fe_3O_4$@MnO/$mSiO_2$—$NH_2$) (16 mg) were incubated with 10 mg EDC and 10 mg NHS for 30 min. Then, anti-CD133 antibodies (1 mL) were added to the mixture and incubated for 1 hour at room temperature. The antibodies-conjugated nanocomposites (MnO/$mSiO_2$-CD133, $Fe_3O_4$@$SiO_2$-CD133 and $Fe_3O_4$@MnO/$mSiO_2$-CD133) were purified by centrifugation at 10,000 rpm for 15 minutes and washed 3-4 times with PBS (pH 7.4).

Particle Characterization

In Vivo MRI Experiments

Adult Sprague-Dawley (SD) rats (8 weeks of age, male, body mass ~300 g) were employed in the experiments. All the animals were fully anesthetized with 5% isoflurane at 1 L min-1 air flow and fitted with a custom designed head holder inside the magnet of a 4.7-Tesla Biospec 47/40 MR scanner. 1-1.5% isoflurane was maintained at 1 L'min-1 air flow throughout the whole experiments. The MRI experiments were performed before and at different times after the injection of three different CAs (Mn-based T1 CA, SPIONP-based T2 CA, DMCA) at a dose of 0.19 mg·$kg^{-1}$ with (T1/T2) TR=500/5000 ms, (T1/T2) TEeff=8/70 ms, FOV=7 cm×7 cm, slice thickness=1.3 mm, and matrix size=256×128 (zero-padded to 256×256) with six repetitions.

Immunostaining and Reverse Transcription-Polymerase Chain Reaction

The animals were deeply anesthetized with an overdose of sodium pentobarbital (60 mg/kg, i.p., Saggittal) and perfused transcardially with fixative (3% paraformaldehyde with 0.1% glutaraldehyde solution in 0.1 M phosphate buffer (PB), pH 7.4) by using peristaltic pump. The brain was then cut into 70 μm sections by using vibratome. Immunofluorescence experiment was performed to label the CD133-expressing NSCs and Glial fibrillary acidic protein (GFAP)-expressing SVZ astrocytes under the laser scan confocal microscope (Olympus fluoview 1000).

The harvested NSCs were collected by magnetic agitation and the total RNA extraction was prepared by a miniprep system (Promega). Reverse transcription polymerase chain reaction (RT-PCR) was then carried out for the determination of the expressions of Sox2, Nanog and Oct4. GAPDH was used as a housekeeping gene for positive control.

In accordance with a first aspect of the present invention, there is provided a real-time method to monitor and harvest stem cells. In particular, the present invention provides a real-time method to monitor and harvest neural stem cells. The present invention has applications in providing an individualized cell replacement therapy for patient in need thereof. More specifically, the present invention has applications in performing real-time monitoring and harvesting of neural stem cells using magnetic resonance imaging (MRI).

In accordance with a second aspect of the present invention, there is provided a contrast agent that can both perform real-time imaging and real-time harvesting of neural stem cells using a magnetic based imaging tool wherein said contrast agent exhibits characteristics comprising strong relaxation property for high contrast imaging; strong magnetic susceptibility for magnetic isolation of neural stem cells; can specifically target and attach to neural stem cells; can harvest said specifically targeted neural stem cells, and high biocompatibility in the human body.

In a first embodiment of the second aspect of the present invention there is provided a contrast agent wherein said magnetic based imaging tool is a magnetic resonance imaging (MRI) apparatus.

In a second embodiment of the second aspect of the present invention there is provided a contrast agent wherein said contrast agent comprising at least one component of a T1 contrast agent and at least one component of a T2 contrast agent.

In a third embodiment of the second aspect of the present invention there is provided a contrast agent wherein said at least one component of T1 contrast agent comprising manganese (Mn) based contrast agents.

In a fourth embodiment of the second aspect of the present invention there is provided a contrast agent wherein said at least one component of T1 contrast agent further comprising magnesium oxide (MnO) based contrast agents.

In a fifth embodiment of the second aspect of the present invention there is provided a contrast agent wherein said at least one component of T2 contrast agent comprising superparamagnetic iron oxide nanoparticles (SPIONPs) based contrast agents.

In a sixth embodiment of the second aspect of the present invention there is provided a contrast agent wherein said at least one component of T2 contrast agent further comprising magnetite ($Fe_3O_4$) and maghemite ($Fe_2O_3$) based contrast agents.

In a seventh embodiment of the second aspect of the present invention there is provided a contrast agent wherein said contrast agent is added to at least one porous silica shell.

In an eighth embodiment of the second aspect of the present invention there is provided a contrast agent wherein said at least one porous silica shell comprising mesoporous silica (mSiO$_2$).

In a ninth embodiment of the second aspect of the present invention there is provided a contrast agent wherein said at least one porous silica shell further comprising at least three distinct topological domains which can be independently functionalized, such as: at least one hollow interior core; one or more worm-like nanochannels, and a silica outmost surface.

In a tenth embodiment of the second aspect of the present invention there is provided a contrast agent wherein the at least one hollow interior core is functionalized with at least one component of the T2 contrast agent.

In an eleventh embodiment of the second aspect of the present invention there is provided a contrast agent wherein the one or more worm-like nanochannels are functionalized with at least one component of the T1 contrast agent.

In a twelfth embodiment of the second aspect of the present invention there is provided a contrast agent wherein the silica outmost surface is functionalized with anti-CD133 antibodies for specific neural stem cells targeting.

In a first embodiment of the third aspect of the present invention there is provided a process of synthesizing the contrast agent according to the second aspect of the present invention wherein an at least one component of a T2 contrast agent is functionalized in an at least one hollow interior core of an at least one porous silica shell, an at least one component of a T1 contrast agent is functionalized in one or more worm-like nanochannels of the at least one porous silica shell, and anti-CD133 antibodies are functionalized on the outer surface of the at least one porous silica shell.

In a second embodiment of the third aspect of the present invention there is provided a process of synthesizing the contrast agent according to the second aspect of the present invention wherein said at least one component of T2 contrast agent comprising superparamagnetic iron oxide nanoparticles (SPIONPs) based contrast agents.

In a third embodiment of the third aspect of the present invention there is provided a process of synthesizing the contrast agent according to the second aspect of the present invention wherein said wherein said at least one component of T2 contrast agent further comprising magnetite (Fe$_3$O$_4$) and maghemite (Fe$_2$O$_3$) based contrast agents.

In a fourth embodiment of the third aspect of the present invention there is provided a process of synthesizing the contrast agent according to the second aspect of the present invention wherein said at least one component of T1 contrast agent comprising manganese (Mn) based contrast agents.

In a fifth embodiment of the third aspect of the present invention there is provided a process of synthesizing the contrast agent according to the second aspect of the present invention wherein said at least one component of T1 contrast agent further comprising magnesium oxide (MnO) based contrast agents.

In a sixth embodiment of the third aspect of the present invention there is provided a process of synthesizing the contrast agent according to the second aspect of the present invention wherein said at least one porous silica shell comprising mesoporous silica (mSiO$_2$).

In a first embodiment of the fourth aspect of the present invention there is provided a method for perform real-time imaging and real-time harvesting of neural stem cells using the contrast agent according to the second aspect of the present invention.

In a second embodiment of the third aspect of the present invention there is provided a method for perform real-time imaging and real-time harvesting of neural stem cells using the contrast agent according to the second aspect of the present invention wherein said magnetic based imaging tool is a magnetic resonance imaging (MRI) apparatus.

INDUSTRIAL APPLICABILITY

The present real-time method to monitor and harvest stem cells is useful in a personalized therapy for regenerating tissues because of permanent damage or lack of suitable replacement, in particular, the real-time method is provided to monitor and harvest neural stem cells in order for collecting multipotent/pluripotent stem cells from the subject who will receive the extracted cells and/or tissues differentiated therefrom in the absence of any invasive surgery or post-treatment against immune rejection. More specifically, the present invention requires using magnetic resonance imaging (MRI) only to perform real-time monitoring and harvesting of neural stem cells based on the contract agents of the present invention which can have dual function/mode.

If desired, the different functions discussed herein may be performed in a different order and/or concurrently with each other. Furthermore, if desired, one or more of the above-described functions may be optional or may be combined.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extent. All publications recited herein are hereby incorporated by reference in their entirety.

What we claim:

1. A dual-mode contrast agent that can both perform real-time imaging and real-time harvesting of neural stem cells using a magnetic based imaging tool, said contrast agent being at least one porous silica shell comprising:
   a) a hollow interior core comprising a T2 contrast agent, wherein the T2 contrast agent is magnetite ($Fe_3O_4$) or maghemite ($Fe_2O_3$) and has an average diameter of 7 nm;
   b) a plurality of worm-like nanochannels;
   c) a T1 contrast agent located within said plurality of worm-like nanochannels, wherein the T1 contrast agent is manganese oxide (MnO) and has an average diameter of 2.5 nm; and
   d) an outmost surface,
   wherein the at least one porous silica shell has an average diameter of 19.5 nm;
   wherein the dual-mode contrast agent is prepared by a method comprising steps of:
   I) contacting tetraethyl orthosilicate (TEOS), with the T2 contrast agent, cetyltrimethylammonium bromide (CTAB), and NaOH in a mixture of chloroform and water thereby loaning a T2@$mSiO_2$ nanoparticle comprising CTAB;
   II) contacting the T2@$mSiO_2$ nanoparticle comprising CTAB with a $MnCl_2$ salt in triethylene glycol thereby forming a T2@$mSiO_2$ nanoparticle comprising CTAB and MnO; and
   III) contacting the T2@$mSiO_2$ nanoparticle comprising CTAB and MnO with ethanol comprising $NH_4NO_3$ thereby forming the dual-mode contrast agent.

2. The dual-mode contrast agent according to claim 1, wherein
   the step I) comprises contacting the T2 contrast agent with the CTAB in the mixture of chloroform and water and then removing the chloroform thereby forming a T2/CTAB solution in water; contacting the T2/CTAB solution with water, CTAB, and NaOH at a temperature of approximately 60° C. thereby forming a T2/CTAB/NaOH solution, and adding the TEOS and ethyl acetate in sequence to the T2/CTAB/NaOH solution thereby forming the T2@$mSiO_2$ nanoparticle comprising CTAB, wherein the mass ratio of the total amount of T2 contrast agent to CTAB to TEOS to NaOH added in step I) is 20:300:470:16;
   the step II) comprises contacting the T2@$mSiO_2$ nanoparticle comprising CTAB with the $MnCl_2$ salt in triethylene glycol at room temperature thereby forming a reaction mixture solution; degassing the reaction mixture solution at 100° C. thereby forming a reaction mixture solution essentially without moisture and oxygen keeping the reaction mixture solution essentially without moisture and oxygen at a temperature of 200° C. for 6 hours; and cooling to room temperature followed by washing with water thereby forming the T2@$mSiO_2$ nanoparticle comprising CTAB and MnO, wherein the $MnCl_2$ salt is $MnCl_2.2H_2O$ and is contacted with the T2@$mSiO_2$ nanoparticle comprising CTAB in a mass ratio of 33:1; and
   the step III) comprises contacting the T2@$mSiO_2$ nanoparticle comprising CTAB and MnO with ethanol containing $NH_4NO_3$ at a temperature of 60° C. for 2 hours and repeating this step twice, and then dialyzing for 48 hours thereby forming the dual-mode contrast agent.

3. The dual-mode contrast agent according to claim 2, wherein said magnetic based imaging tool is a magnetic resonance imaging (MRI) apparatus.

4. The dual-mode contrast agent according to claim 2, wherein said T2 contrast agent is a superparamagnetic iron oxide nanoparticle (SPIONP) based contrast agent.

5. The dual-mode contrast agent according to claim 2, wherein said plurality of worm-like nanochannels are about 2.5 nm in diameter.

6. The dual-mode contrast agent according to claim 2, wherein the silica outmost surface is functionalized with anti-CD133 antibodies.

7. The dual-mode contrast agent according to claim 6, wherein said anti-CD133 antibodies are covalently attached to said silica outmost surface with a linker comprising a propyl amine.

8. The dual-mode contrast agent according to claim 1, wherein the method further comprises the step of contacting the T2@$mSiO_2$ nanoparticle comprising CTAB and MnO, 3-amino-propyltrimethoxysilane, and $NH_4OH$ in ethanol and water prior to step III).

9. The dual-mode contrast agent according to claim 1, wherein the step I) comprises contacting the T2 contrast agent with the CTAB in the mixture of chloroform and water and then removing the chloroform thereby forming a T2/CTAB solution in water; contacting the T2/CTAB solution with water, CTAB, and NaOH at a temperature of approximately 60° C. thereby forming, a T2/CTAB/NaOH solution; and adding the TEOS anti ethyl acetate in sequence to the T2/CTAB/NaOH solution thereby forming the T2@$mSiO_2$ nanoparticle comprising CTAB.

10. The dual-mode contrast agent according to claim 1, wherein the step II) comprises contacting the T2@$mSiO_2$ nanoparticle comprising CTAB with the $MnCl_2$ salt in triethylene glycol at room temperature thereby forming a reaction mixture solution; degassing the reaction mixture solution at 100° C. thereby forming a reaction mixture solution essentially without moisture and oxygen; keeping the reaction mixture solution essentially without moisture and oxygen at a temperature of 200° C. for 6 hours; and cooling to room temperature followed by washing with water thereby forming the T2@$mSiO_2$ nanoparticle comprising CTAB and MnO.

11. The dual-mode contrast agent according to claim 1, wherein in the step III) comprises contacting the T2@$mSiO_2$ nanoparticle comprising CTAB and MnO with ethanol containing $NH_4NO_3$ at a temperature of 60° C. for 2 hours and repeating this step twice; and then dialyzing for 48 hours thereby forming the dual-mode contrast agent.

12. The dual-mode contrast agent according to claim 8, wherein in the step I) comprises contacting the T2 contrast agent with the CTAB in the mixture of chloroform and water and then boiling off the chloroform thereby forming a T2/CTAB solution; contacting the T2/CTAB solution with water, CTAB and NaOH at a temperature of approximately 60° C. thereby forming a T2/CTAB/NaOH solution; adding the TEOS and ethyl acetate in sequence to the T2/CTAB/NaOH solution thereby forming the T2@$mSiO_2$ nanoparticle comprising CTAB.

13. The dual-mode contrast agent according to claim 12, wherein the step II) comprises contacting the T2@$mSiO_2$ nanoparticle comprising CTAB with the $MnCl_2$ salt in triethylene glycol at room temperature thereby forming a reaction mixture solution; degassing the reaction mixture solution at 100° C. thereby forming a reaction mixture solution essentially without moisture and oxygen; keeping the reaction mixture solution essentially without moisture and oxygen at a temperature of 200° C. for 6 hours; and cooling to room temperature followed by washing with distilled water thereby forming the T2@mSiO$_2$ nanoparticle comprising CTAB and MnO.

14. The dual-mode contrast agent according to claim 13, wherein the step III) comprises contacting the T2@mSiO$_2$ nanoparticle comprising CTAB and MnO with ethanol containing NH$_4$NO$_3$ at a temperature of 60° C. for 2 hours and repeating this step twice, and then dialyzing for 48 hours thereby forming the dual-mode contrast agent.

15. The dual-mode contrast agent of claim 2, wherein said contrast agent exhibits characteristics comprising:
   a) strong relaxation property for high contrast imaging provided by at least one component of the T1 contrast agent in the plurality of worm-like nanochannels;
   b) strong magnetic susceptibility for magnetic isolation of neural stem cells provided by at least one component of the T2 contrast agent in the hollow interior core;
   c) capability to specifically target and attach to neural stem cells via antibodies functionalized in/on the outmost surface; or
   d) capability to harvest said specifically targeted neural stem cells using said antibodies and T1/T2 contrast agents, wherein said antibodies, T1/T2 contrast agents, or both exhibit high biocompatibility in the human body.

* * * * *